United States Patent [19]

Kingston et al.

[11] Patent Number: 5,739,359
[45] Date of Patent: Apr. 14, 1998

[54] METHODS FOR PREPARING 1-DEOXY PACLITAXELS

[75] Inventors: David G. I. Kingston, Blacksburg; Mahendra D. Chordia, Charlottesville; Prakash G. Jagtap, Blacksburg, all of Va.

[73] Assignee: Virginia Tech Intellectual Properties, Inc., Blacksburg, Va.

[21] Appl. No.: 840,171

[22] Filed: Apr. 14, 1997

Related U.S. Application Data

[63] Continuation-in-part of Ser. No. 788,274, Jan. 24, 1997.
[51] Int. Cl.[6] .................... C07D 309/08; C07D 305/14
[52] U.S. Cl. ..................... 549/358; 549/510; 549/511
[58] Field of Search ........................... 549/510, 511, 549/358

[56] References Cited

PUBLICATIONS

Ojima et al., "New and Efficient Approaches to the Semi-synthesis of Taxol and Its C–13 Side Chain Analogs by Means of β–Lactam Synthon Methods" *Tetrahedron* (1992) 48:6985–7012, No. 34.

Brieva et la., "Chemoenzymatic Synthesis of the C–13 Side Chain of Taxol: Optically–Active 3–Hydroxy–4–phenyl β–Lactam Derivatives" *J. Org. Chem.* (1993) 58:1068–1075, No. 5.

S.H. Chen, "The Chemistry of Taxanes: Skeletal Rearrangements of Baccatin Derivatives via Radical Intermediates," *J. Org. Chem.* (1994) 56:1475–1484.

A.G. Chaudhary et al., "A Novel Benzoyl Group Migration: Synthesis and Biological Evaluation of 1–Benzoyl–2–des(benzoyloxy)paclitaxel," *J. Org. Chem.* (1995) 60:3260–3262.

*Primary Examiner*—Ba K. Trinh
*Attorney, Agent, or Firm*—Burns, Doane, Swecker & Mathis, L.L.P.

[57] ABSTRACT

The present invention provides methods for making a novel class of 1-deoxy paclitaxel derivatives. These derivatives include 1-deoxy paclitaxel. The derivatives of the present invention are potent cytotoxic agents.

11 Claims, No Drawings

METHODS FOR PREPARING 1-DEOXY PACLITAXELS

CROSS REFERENCE TO RELATED APPLICATION

This application is a continuation-in-part of U.S. application Ser. No. 08/788,274 filed Jan. 24, 1997.

FIELD OF THE INVENTION

The present invention is directed to methods for making novel antitumor compounds. More particularly, the invention provides novel synthetic routes for preparing 1-deoxy paclitaxel derivatives, which are potent cytotoxic agents.

BACKGROUND OF THE INVENTION

Paclitaxel is a natural product extracted from the bark of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," *Pharmac. Ther.*, 52:35–84, 1991; by several authors in the book "Paclitaxel in Cancer Treatment" edited by McGuire and Rowinsky, 1995, Marcel Dekker Inc., New York, N.Y., 121–338; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; by K. C. Nicolaou et al. in "Chemistry and Biology of Taxol," *Angew. Chem., Int. Ed. Engl.*, 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been reported to have good antitumor activity. The structures of paclitaxel and Taxotere® are shown below along with the conventional numbering system for molecules belonging to the class; such numbering system is also employed in this application.

Taxol®: R=Ph; R'=acetyl
Taxotere®: R=t-butoxy; R'=hydrogen

SUMMARY OF THE INVENTION

This invention relates to methods for making novel antitumor compounds represented by formula I, or pharmaceutically acceptable salts thereof wherein R is hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, cyclic 3–7 membered ring containing either one or two heteroatoms, heteroaryl or $-Z^1-R^3$;

$Z^1$ is a direct bond, $C_{1-6}$ alkyl, or $O-C_{1-6}$ alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ and $R^B$ are independently hydrogen, $-HNC(O)R$, $-NHC(O)OR$, $-NHC(O)NHR$, $-NHC(O)N(R)_2$, $-NHS(O)_mR$, $-NHP(=O)(OR)_2$, $NHP=S(OR)_2$, where m is 1 or 2;

$R^C$ and $R^D$ are independently hydrogen, hydroxy, fluoro, $-OC(O)R^x$, $-OC(O)OR^x$, $OP(O)(OH)_2$, $OCH_2OP(O)(OH)_2$, $OCH_2OCH_2OP(O)(OH)_2$, $-(OCH_2)_nOC(O)CH_2NHR^x$, $-(OCH_2)_nOC(O)CH_2NHR'_6R'_7$ where n is $0-3$, $-OCOCH_2CH_2NH_3{}^+HCOO^-$, $-OCOCH_2CH_2COOH$, $-OCO(CH_2)_3COOH$, $OC(O)(CH_2)_nNR^FR^G$, where n is 0–3, $-OC(O)CH(R')NH_2$, $OC(O)CH_2CH_2C(O)OCH_2CH_2OH$ or $-OC(O)-Z-C(O)-$;

Z is ethylene ($-CH_2CH_2-$), propylene ($-CH_2CH_2CH_2-$), $-CH=CH-$, 1,2-cyclohexane or 1,2-phenylene; R' is $-OH$, OH base, $-NR'_2R'_3$, $-OR'_3$, $SR'_3$, $-OCH2C(O)NR'_4R'_5$;

$R'_2$ is $-H$ or $-CH_3$;

$R'_3$ is $-CH_2NHR'_6R'_7$ or $-CH_2N^+R'_6R'_7R'_8X^-$, where n is 1–3;

$R'_4$ is $-H$ or $-C_1-C_4$ alkyl;

$R'_5$ is $-H$, $-C_1-C_4$ alkyl, benzyl, hydroxyethyl, $-CH_2CO_2H$ or dimethylamino;

$R'_6$ and $R'_7$ are independently $-H$, $-CH_3$, $-CH_2CH_3$, benzyl or $R'_6$ and $R'_7$ together with the nitrogen of $NR'_6R'_7$ form a pyrrolidino, piperidino, morpholino, or N-methylpiperazino group;

$R'_8$ is $-CH_3$, $-CH_2CH_3$, or benzyl;

$X^-$ is halide;

base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH;

$R^F$ and $R^G$ are independently $-H$ or $-C_1-C_3$ alkyl, or $R^F$ and $R^G$ taken together with the nitrogen of $NR^FR^G$ form a pyrrolidino, piperidino, morpholino, or N-methylpiperazino group;

R" is $-H$, or $C_{1-6}$ alkyl;

$R^2$ is $R^x$, $R^y$, or $R^y$;

$R^4$ is $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ heteroaryl, $-O-C_{1-6}$ alkyl, $-O-C_{2-6}$ alkenyl, $-O-C_{2-6}$ alkynyl, —CH$_2$OCH$_3$, —CH$_2$OCH$_2$OCH$_3$, —CH$_2$OCH$_2$OCH$_2$CH$_3$, —CH$_2$CH$_2$OCH$_3$, —CHOCH$_2$ (an oxirane), or —S—C$_{1-6}$ alkyl;

L is O or S;

R$^6$ and R$^{6'}$ are hydrogen;

R$^{7'}$ is hydrogen; R$^7$ is hydroxy, —OC(O)R$^x$, —OC(O)OR$^x$, O—C$_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$;

R$^9$ and R$^{9'}$ are independently hydrogen, hydroxy, —OC(O)R$^x$, —OC(O)OR$^x$, O—C$_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$;

R$^{10}$ and R$^{10'}$ are independently hydrogen, hydroxy, —OC(O)R$^x$, —OC(O)OR$^x$, O—C$_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$;

R$^{14}$ is hydrogen,

R$^{19}$ is methyl, hydroxymethyl, or R$^{19}$ and R$^7$ together can form a cyclopropane ring with the proviso that when these substituents are cyclopropane then R$^{7'}$ is hydrogen;

R$^x$ is C$_{1-6}$ alkyl, C$_{2-6}$ alkenyl, C$_{2-6}$ alkynyl, C$_{3-6}$ cycloalkyl, any of which groups can be optionally substituted with one to six of the same or different halogen atoms;

R$^y$ is a radical of the formula

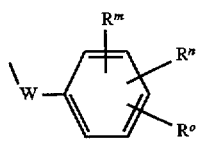

wherein W is a bond and R$^m$, R$^n$, and R$^o$ are independently hydrogen, nitro, cyano, azido, amino, C$_{1-6}$ alkylamino, di-C$_{1-6}$ alkylamino, halogen, C$_{1-6}$ alkyl, hydroxy, or C$_{1-6}$ alkyoxy; and R$^{y'}$ is a radical of the formula

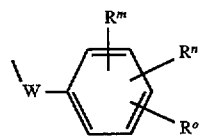

wherein W is C$_{1-6}$ alkyl or —OC$_{1-6}$ alkyl and R$^m$, R$^n$, and R$^o$ are independently hydrogen, nitro, cyano, azido, amino, C$_{1-6}$ alkylamino, di- C$_{1-6}$ alkylamino, halogen, C$_{1-6}$ alkyl, hydroxy, or C$_{1-6}$ alkyoxy.

The methods involve manipulations of 1-deoxybaccatin VI; particularly the addition of the paclitaxel C-13 side chain, and variations thereof, to 1-deoxybaccatin VI by reaction of a 13-deacetyl-1-deoxybaccatin derivative with a β-lactam, preferably a 3-hydroxy-4-phenyl β-lactam or derivatives thereof having a hydroxy protecting group at the C-3 position. These synthetic routes avail syntheses of a class of 1-deoxypaclitaxels that have potent cytotoxic effects.

Another aspect of the present invention provides a method for reversing or inhibiting tumor growth in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group contains. For example "C$_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "C$_{1-6}$ alkyl" can also refer to C$_{1-6}$ alkylene which bridges two groups; examples include propane-1,3-diyl, butane-1,4-diyl, 2-methyl-butane-1,4-diyl, etc. "C$_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "C$_{2-6}$ alkenyl" can also refer to C$_{2-6}$ alkenediyl which bridges two groups; examples include ethylene-1,2-diyl (vinylene), 2-methyl-2-butene-1,4-diyl, 2-hexene-1,6-diyl, etc. "C$_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from C$_{1-6}$ alkanoyloxy, hydroxy, halogen, C$_{1-6}$ alkyl, trifluoromethyl, C$_{1-6}$ alkoxy, aryl, C$_{2-6}$ alkenyl, C$_{1-6}$ alkanoyl, nitro, amino, cyano, azido, C$_{1-6}$ alkylamino, di-C$_{1-6}$ alkylamino, and amido. "Halogen" means an atom or radical selected from among fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

The term "hydroxy protecting groups" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis.*, 2d Ed., 1991, John Wiley & Sons, and McOmie *Protective Groups in Organic Chemistry*, 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy; halogen such as chloro or fluoro; nitro; amino; and keto.

The term "taxane", "taxane tetracyclic nucleus" or "taxane core" refers to moieties with a framework of the structure:

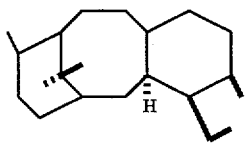

The cyclopropane group, which can be constituted from $R^7$ and $R^{19}$ of formula I can alternatively be referred to as "7b,8b-methano" group as in Tetrahedron Letters, Vol. 35, No. 43, pp 7893–7896 (1994) or as "cyclopropa" group as in U.S. Pat. No. 5,254,580 issued Oct. 19, 1993.

Preferred embodiments include compounds with the structure II, or pharmaceutically acceptable salts thereof, having the following groups: $R^A$=-hydrogen, $R^C$=-hydrogen, $R^{10'}$=-hydrogen, $R^{7'}$-hydrogen, $R^6$=$R^{6'}$=-hydrogen, $R^{14}$=-hydrogen

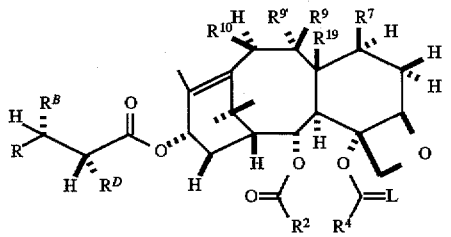

R includes 2-furanyl, (2-furyl), 2-thienyl, 3-furanyl (3-furyl), 3-thienyl, phenyl, 4-methylphenyl, naphthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl, and the like.

$R^B$ includes —NHC(O)Ph (or substituted phenyl),—NHC(O)O($C_{1-6}$ alkyl), most preferably —NHC(O))'Bu, —NHC(O)OnBu, —NHC(O)OiPr, —NHC(O)OCH$_2$Ph, —NHC(O)-heterocycle, including —NHC(O)-2-furyl, —NHC(O)NHR, —NHC(O)N(R)$_2$;

$R^D$ includes hydroxy, OP(O)(OH)$_2$, OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)CH$_3$, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R';

$R^2$ includes -phenyl or substituted phenyl (preferably with mono or bis meta or ortho substitution);

L is oxygen or sulfur;

$R^4$ includes most preferably methyl, but can also be $C_{1-4}$ alkyl, $C_{3-5}$ cycloalkyl, —O—$C_{1-4}$ alkyl, —CH$_2$OCH$_3$, —CHOCH$_2$ (an oxirane), or —S—$C_{1-4}$ alkyl;

$R^7$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R'; most preferably $R^7$ is hydrogen, hydroxy, —OC(O)CH$_3$, or a group linking $R^7$ and $R^{9'}$. The linking groups can be —OCH$_2$O—, —OCH(R$^H$)O—, —OCR$^H$R$^I$O—, and —OC(O)O—;

$R^H$ is preferably methyl or phenyl and $R^I$ is preferably methyl. Alternatively, $R^H$ and $R^I$ can include $C_{1-6}$ alkyl, $C_{1-6}$ cycloalkyl, and aryl. Together, $R^H$ and $R^I$ can be —(CH$_2$)$_n$—, where n=3–5.

$R^9$ is hydrogen, or alternatively $R^9$ and $R^{9'}$ together can be oxygen (an oxo group). If $R^{9'}$ is hydrogen, $R^9$ can be hydroxyl.

$R^{9'}$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R'; most preferably $R^{9'}$ is hydrogen, hydroxy, —OC(O)CH$_3$, or a group linking $R^7$ and $R^{9'}$. The linking groups can be —OCH$_2$O—, —OCH(R$^H$)O—, —OCR$^H$R$^I$O—, and —OC(O)O—;

$R^{10}$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3, —OC(O)CH(R')NH$_2$, OC(O)CH$_2$CH$_2$C(O)OCH$_2$CH$_2$OH or —OC(O)—Z—C(O)—R'; most preferably $R^{10}$ is hydrogen, hydroxy, or —OC(O)CH$_3$.

$R^{19}$ is —CH$_3$, or $R^{19}$ and $R^7$ together can form a cyclopropane ring with the proviso that when these substituents are a cyclopropane ring, then $R^{7'}$ is hydrogen.

Other preferred embodiments include compounds with the structure III, or pharmaceutically acceptable salts thereof, having the following groups:

$R^A$=-hydrogen, $R^C$=-hydrogen, $R^2$=-phenyl, $R^4$=-methyl, $R^6$=$R^{6'}$=-hydrogen, $R^{7'}$=-hydrogen, $R^{9'}$=-hydrogen, $R^{10'}$=-hydrogen, L=oxygen, $R^{14}$=-hydrogen, $R^{19}$=$CH_3$.

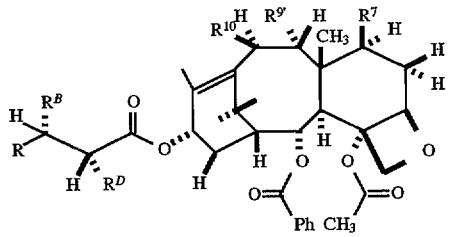

This depiction will be used to describe the specific experimental procedures of the invention, but in no way implies that the other compounds encompassed by the invention are not amenable to the procedures described herein. The structures I=II=III except that some of the variables in I are assigned as above to produce III. The structures are intended to be derivatives of the generic structure I in which the substituents above have been assigned for clarity in the examples. Concise methods for synthesizing other generic compounds of Structure I not encompassed by specified formula III are described in the text and are well known in the art.

R includes 2-furanyl, (2-furyl), 2-thienyl, 3-furanyl (3-furyl), 3-thienyl, phenyl, naphthyl, 4-hydroxyphenyl, 4-methoxyphenyl, 4-fluorophenyl, 4-trifluoromethylphenyl, 2-propynyl, benzyl, phenethyl, phenylehthenyl, 3,4-dimethoxyphenyl, 2-(2-furanyl)ethenyl, 2-methylpropyl, $C_{3-6}$ cycloalkyl, cyclohexylmethyl, cyclohexylethyl, and the like.

$R^B$ includes —NHC(O)Ph (or substituted phenyl), —NHC(O)O($C_{1-6}$ alkyl), most preferably —NHC(O))$^t$Bu, —NHC(O)OnBu, —NHC(O)OiPr, —NHC(O)OCH$_2$Ph, —NHC(O)-heterocycle, including —NHC(O)-2-furyl, —NHC(O)NHR, —NHC(O)N(R)$_2$;

$R^D$ includes hydroxy, OP(O)(OH)$_2$, OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)CH$_3$, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R';

$R^7$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R'; most preferably $R^7$ is hydrogen, hydroxy, —OC(O)CH$_3$, or a group linking $R^7$ and $R^{9'}$. The linking groups can be —OCH$_2$O —, —OCH(R$^H$)O—, —OCR$^H$R'O—, and —OC(O)O—;

$R^H$ is preferably methyl or phenyl and $R^I$ is preferably methyl. Alternatively, $R^H$ and $R^I$ can include $C_{1-6}$ alkyl, $C_{1-6}$ cycloalkyl, and aryl. Together, $R^H$ and $R^I$ can be —(CH$_2$)$_n$—, where n=3–5.

$R^9$ is hydrogen, or alternatively $R^9$ and $R^{9'}$ together can be oxygen (an oxo group). If $R^{9'}$ is hydrogen, $R^9$ can be hydroxyl.

$R^{9'}$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R'; most preferably $R^{9'}$ is hydrogen, hydroxy, —OC(O)CH$_3$, or a group linking $R^7$ and $R^{9'}$. The linking groups can be —OCH$_2$O—, —OCH(R$^H$)O—, —OCR$^H$R'O—, and —OC(O)O—;

$R^{10}$ includes hydrogen, hydroxy, —O—$C_{1-6}$ alkyl, —OC(O)CH$_3$, OC(O)R$^x$, —OC(O)OR$^x$, —OC(O)NHR$^x$, —OC(O)NR$_2$, OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, OCH$_2$SR, most preferably —OCH$_2$SCH$_3$, or —OCH$_2$OCH$_2$SCH$_3$, —OC(R$^x$)$_2$SR, —OCHR$^x$SR, —OP(O)(OH)$_2$, —OCH$_2$OP(O)(OH)$_2$, OCH$_2$OCH$_2$OP(O)(OH)$_2$, —(OCH$_2$)$_m$OC(O)CH$_2$NHR$^x$, —(OCH$_2$)$_m$OC(O)CH$_2$NHR'$_6$R'$_7$ where m is 0–3, —OC(O)OCH$_2$CCl$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH, —OCO(CH$_2$)$_3$COOH, OC(O)(CH$_2$)$_n$NR$^F$R$^G$, where n is 0–3,—OC(O)CH(R')NH$_2$, OC(O)CH$_2$CH$_2$C(O)OCH$_2$CH$_2$OH or —OC(O)—Z—C(O)—R'; most preferably $R^{10}$ is hydrogen, hydroxy, or —OC(O)CH$_3$.

The methods of the present invention include a method for preparing 1-deoxy-7,9-acetonide paclitaxel analogues comprising: (a) deacetylating 1-deoxybaccatin VI to form a 7,9,10-trisdeacetyl derivative; (b) modifying the 7,9,10-trisdeacetyl derivative to form a 7,9-acetonide derivative; (c) protecting an hydroxy substituent at C-10 of 1-deoxybaccatin VI with a hydroxy protecting group; (d) forming a C-13 deacetyl derivative of the product of step (c); (e) esterifying the C-13 deacetyl derivative of step (d) by reaction with a 3-hydroxy-4-phenyl β-lactam, wherein the 3-hydroxy group is protected with a protecting group; (f) and deprotecting both the C-2' position resulting from step (e), and the C-10 position. Preferably, the β-lactam is N-t-butoxy-3-triisopropylsilyloxy-4-phenyl β-lactam; the hydroxy protecting groups are the same or different and are trialkylsilyl protecting groups; and the acetonide is formed by reacting the product of step (a) with 2-methoxypropene.

The present invention provides a method for preparing 1-deoxy-7,9-benzylidene acetal paclitaxel analogues comprising: (a) deacetylating 1-deoxybaccatin VI to form a 7,9,10-trisdeacetyl derivative; (b) modifying the 7,9,10-trisdeacetyl derivative to form a 7,9-benzylidene acetal derivative; (c) protecting an hydroxy substituent at C-10 of 1-deoxybaccatin VI with a hydroxy protecting group; (d) forming a C-13 deacetyl derivative of the product of step (c); (e) esterifying at the C-13 position of the deacetyl derivative of step (d) by reaction with a 3-hydroxy-4-phenyl β-lactam, wherein the 3-hydroxy substituent is protected with a hydroxy protecting group; and (f) deprotecting both the C-2' position resulting from step (e), and the C-10 position. Preferably, the β-lactam is N-t-butoxy-3-tetrabutyldimethylsilyloxy-4-phenyl β-lactam; the hydroxy protecting groups of steps (c) and (e) are the same or different and are trialkylsilyl protecting groups; and the 7,9-benzylidene acetal of step (b) is formed by reacting the product of step a with benzaldehyde.

The present invention provides a method for forming 1-deoxy docetaxel comprising: (a) selectively denying an acetoxy group from C-13 of 1-deoxybaccatin VI to form 13-deacetyl-1-deoxybaccatin VI; (b) coupling the product of step (a) with a 3-silyl ester-4-phenyl β-lactam to form a C-13 ester; and (c) deacetylating the 7, 9, and 10 positions of the product of step (b). Preferably, the β-lactam is N-t-butoxy-3-tetrabutyldimethylsilyloxy-4-phenyl β-lactam.

The present invention also provides a method for forming 7,9-diacetyl-1-deoxy-9(R)-dihydropaclitaxel comprising: (a) selectively cleaving an acetoxy group from C-13 of 1-deoxybaccatin VI to form 13-deacetyl-1-deoxybaccatin VI; (b) coupling the product of step (a) with N-benzyl-3-triethylsilyloxy-4-phenyl β-lactam to form an ester at C-13; and (c) selectively removing the triethylsilyl hydroxy protecting group from C-2' of the product of step (b).

The new products that have the general formula selected from among I, II, and III display a significant inhibitory effect on abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by the methods disclosed herein and techniques from the conventional organic chemistry repertoire. Schemes 1-3, which depict processes by which compounds within the scope of formula I can be made, are only shown for the purpose of illustration and are not to be construed as limiting the processes to make the compounds by any other methods.

The following procedures describe methods which can be utilized to prepare taxane analogs which are deoxygenated at C-1 and which have surprisingly unexpected anticancer properties. The synthesis and unexpected enhanced properties of taxane analogs which are deoxygenated at the C-1 position has never before been disclosed. Several investigators have attempted to deoxygenate paclitaxel at the C-1 position, but none of these have been successful. See for example Chaudhary et al., *J. Org. Chem.* 60: 3260–3262, 1995, and Chen et al., *J. Org. Chem.* 59: 1475–1484, 1994. The contemplated analogs can be prepared from 1-deoxybaccatin VI (1) by the methods described herein:

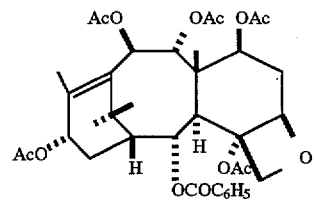

1-Deoxybaccatin VI is a known diterpenoid that has been isolated from *Taxus mairei*: Min, Z. D., Jiang, H., and Liang, J. Y., Taxane diterpenes of the heartwood from *Taxus mairei*, *Acta Pharm. Sin (Yaoxue Xuebao)*, 24: 673–677, 1989. This material is useful in the synthesis of 1-deoxypaclitaxel analogs by the methods described herein. The methods are described more fully in Schemes 1-3.

The β-lactam synthons 8a and 8b were prepared by the method of Ojima et al., *Tetrahedron*, 48, pp 6985–7012 (1992).

Preparation of 10-Deacetyl-1-deoxy-9-dihydropaclitaxel-7,9-acetonide (7a) (Scheme 1)

Several approaches are possible for the synthesis of 1-deoxypaclitaxel analogs from 1-deoxybaccatin VI (1). In the first approach, shown in Scheme 1, 1-deoxybaccatin VI was treated with Triton B® to give the 7, 9, 10-trisdeacetyl derivative 2a in good yield. The use of Triton B® in this step gives a selective method for deacetylating the 7, 9, and 10 positions selectively without significant deacylation of the 2, 4, and 13 positions.

The triol 2a (as a crude mixture with a minor by-product of the initial reaction) was then protected at the 7 and 9 positions by formation of the acetonide derivative 3a by treatment with 2-methoxypropene and pyridinium tosylate at room temperature. This reaction only forms the acetonide derivative between the 7 and 9 hydroxyl groups; no acetonide formation was observed between the 9 and 10 hydroxyl groups because of the unfavorable stereochemistry for this reaction. Compound 3a was obtained in 51% overall yield from 1.

Treatment of the acetonide 3a with triethylsilyl chloride in dichloromethane with imidazole as a catalyst gave the protected 10-(triethylsilyl) derivative 4a. Treatment of this compound with methyllithium gave a clean deacylation of the C-13 acetyl group to give the key intermediate 5a.

Conversion of 5a to the paclitaxel analog 7a was carried out in two steps. In the first step the β-lactam 8a was reacted with 5a in the presence of butyllithium to form the 13-alkoxide salt of 5a. This procedure gave the coupled product 2'-tetrabutyldimethylsilyl-10-deacetyl-1-deoxy-10-triethylsilyl-9-dihydro -9(R) -paclitaxel 7,9-acetonide (6a) in moderate yield (23%), but later experience suggests that this yield can be improved with careful control of the conditions. In the final step, compound 6a was deprotected with HF and pyridine to give the product 10-deacetyl-1-deoxy-9-dihydropaclitaxel-7,9-acetonide (7a).

Preparation of 1-deoxy-9(R)-dihydrodocetaxel 7,9-benzylidene acetal (7b) (Scheme 2)

Treatment of the triol 2a (Scheme 1) with benzaldehyde in the presence of camphor sulfonic acid and molecular sieves in toluene gave the benzylidene acetal 3b in 63% yield, and protection of the C-10 hydroxyl group with triethylsilyl chloride in dichloromethane with imidazole as a catalyst gave the protected 10-(triethylsilyl) derivative 4b.

Careful treatment of 4b with methyllithium in THF gave the 13-deacetyl derivative 5b in 37% yield.

Treatment of the 13-hydroxy derivative 5b with the β-lactam 8b in the presence of sodium hydride to form the 13-alkoxide salt gave the coupled intermediate 6b in 69% yield. Deprotection of 6b with HF and pyridine gave the final product 7b in 33% yield.

Preparation of 7,9,10-triacetyl-1-deoxy-9(R)-dihydrodocetaxel (7c) (Scheme 3)

Treatment of 1-deoxybaccatin VI (1) with sodium bis(2-methoxyethoxy)aluminum hydride in toluene (RedAl, (Aldrich Chemical Company) gave a highly efficient and unexpectedly selective cleavage of the C-13 acetoxy group to give 13-deacetyl-1-deoxybaccatin VI (2c) in 77% yield, together with small amounts of a second product tentatively identified as 4-deacetyl-1-deoxybaccatin VI (2b).

Coupling of 2c with the β-lactam 8a gave the coupled product 6c in 77% yield. Deprotection of 6c with HF and pyridine gave the desired product 7,9,10-triacetyl-1-deoxy-9(R)-dihydrodocetaxel (7c) in 96% yield.

Preparation of 1-deoxy-9(R)-dihydrodocetaxel (7d) (Scheme 3)

Treatment of the intermediate 6c from the previous experiment with Triton B in dichloromethane gave the intermediate 6d. Deprotection of 6d with tetrabutylammonium fluoride in THF gave 1-deoxy-9(R)-dihydrodocetaxel (7d) in 80% yield.

Some of the schemes refer to a hydroxy protecting group, preferably a trialkylsilyl group. It is to be understood that hydroxy protecting group may also be a carbonate or ester group —C(O)OR$^x$ or —C(O)R$^x$. Thus when such a group is employed as a hydroxy protecting group, it may either be removed to generate the free hydroxy protecting group or it may remain as a part of the final product. By now there are many publications teaching the introduction of a wide variety of groups onto a taxane core. By using these well established methods or obvious variants thereof, the starting taxanes of formula VII, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for convening C2-benzoyloxy to other groups see, A. G. Chaudhary et al., *J. Am. Chem. Soc.* 116, pp 4097–4098 (1994); S. H. Chen et al, *Bioorganic and Medicinal Chemistry Letters*, Vol. 4, No. 3, pp 479–482 (1994); K. C. Nicolaou et al., *J. Am. Chem. Soc.*, 1995, 117, 2409 and European Patent Application 617,034A1 published Sep. 28, 1994; for modifying C10-acetyloxy see, K. V. Rao et al., *J. Med. Chem.*, 38, pp 3411–3414 (1995), J. Kant et al., *Tetrahedron Letters*, Vol. 35, No. 31, pp 5543–5546 (1994); and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making C-10 epi hydroxy or acyloxy compounds see PCT application WO 96/03394; for making C-10 deoxy-C-10 alkyl analogs see PCT application WO 95/33740; for making 7b,8b-methano, 6a,7a-dihydroxy and 6,7-olefinic groups see, R. A. Johnson, *Tetrahedron Letters*, Vol. 35, No. 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, *Tetrahedron Letters*, Vol. 36, No. 17, pp 2901–2904 (1995); for making C7-epi-fluoro see, G. Roth et al, *Tetrahedron Letters*, Vol. 36, pp 1609–1612 (1995); for forming C7 esters and carbonates see, U.S. Pat. No. 5,272, 171 issued Dec. 21, 1993 and S. H. Chen et al., *Tetrahedron*, 49, No. 14, pp 2805–2828 (1993); for 9a- and 9b-hydroxy taxanes see, L. L. Klein, *Tetrahedron Letters*, Vol. 34, No. 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg et. al., *Tetrahedron Letters*, Vol. 36, No. 11, pp 1783–1786 (1995).

DESCRIPTION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); (DHQ)$_2$PHAL (hydroquinine 1,4-phthalazinediyl diether). Tf=triflate=trifluoromethanesulfonate; LRMS (low resolution mass spectrometry); ESI (electrospray ionization).

EXAMPLE 1

(Scheme 1)

Preparation of 10-Deacetyl-1-deoxy-9-dihydropaclitaxel-7,9-acetonide (7a)

7,9,10-Trideacetylbaccatin VI (2a): To a solution of 1-deoxybaccatin VI 1 (15.00 mg, 0.021 mmol.) in MeOH (2.0 mL) was added 1N NaOH (120 mL) at 0° C. and the reaction mixture was stirred at room temperature for 4 h. $CO_2$ was bubbled through the reaction mixture and the residue obtained after evaporation was purified by PTLC (silica gel, 500 mm, EtOAc/hexane 3/2) to yield 2a (9.00 mg, 84%). $^1$H-NMR (400 MHz, CDCl$_3$): d 1.20 (s, 3H), 1.63–1.69 (m, 1H), 1.76 (s, 3H), 1.79 (s, 3H), 1.85 (s, 6H), 1.88–1.96 (m, 2H), 2.18 (s, 3H), 2.27 (s, 3H), 2.42–2.61 (m, 2H), 2.88 (d, J=5.96 Hz, 1H), 3.08 (s, 1H), 3.42 (s, 1H), 4.16 (d, J=8.39 Hz, 1H), 4.32–4.41 (m, 3H), 4.76 (s, 1H), 4.91 (d, J=10.38 Hz, 1H), 4.98 (d, J=8.09 Hz, 1H), 5.75 (dd, J=2.14 and 5.95 Hz, 1H), 5.96 (d, J=10.5 Hz, 1H), 7.48 (t, J=7.94 Hz, 2H), 7.59 (t, J=7.32 Hz, 1H), 8.05 (dd, J=8.39 and 1.2 Hz, 2H). $^{13}$C NMR (400 MHz, CDCl$_3$): (12.46, 14.84, 21.27, 22.79, 26.68, 26.84, 31.70, 38.13, 38.18, 44.09, 44.32, 47.23, 69.34, 71.21, 71.68, 74.48, 78.78, 81.76, 83.89, 128.56, 129.75, 133.48, 135.29, 137.38, 164.99, 169.26, 170.66.

7,9,10-Trideacetylbaccatin VI (2a) (alternate method): To a solution of 1-deoxy-baccatin VI 1 (67 mg, 0.095 mmol.) in anhydrous CH$_2$Cl$_2$ (1.0 mL) was added benzyltrimethyl ammonium hydroxide (45 mL, 40% w/w solution in methanol, 0.1 mmol, Triton B⓪ at 0° C. The reaction mixture was stirred at room temperature and the progress of the reaction was monitored by TLC until formation of a new polar material appeared to be complete. The reaction mixture was diluted with cold CH$_2$Cl$_2$ (5 mL) at 0° C., and quenched with 0.1N HCl (5 mL). The organic layer was separated, washed successively with water, saturated NaHCO$_3$, and brine, and dried over Na$_2$SO$_4$. Concentration of the organic layer under reduced pressure gave crude residue, which was purified by PTLC (silica gel, 1000 mm, EtOAc/hexane, 3:2) to yield a mixture (55 mg) of 2a along with a minor amount of a UV-inactive compound which was not characterised. This crude mixture was used directly for the next step.

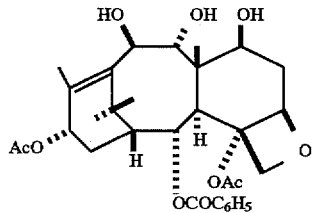

2a 7,9,10-Trideacetylbaccatin VI 7,9-acetonide (3a): To a solution of the mixture obtained from the above reaction (55 mg) in CH$_2$Cl$_2$ (3 mL), 2-methoxy propene (10 mL, 1.0 mmol.) and pyridinium tosylate (2 mg) were added and the solution stirred at room temperature for 12 h. After completion of the reaction, the mixture was diluted with CH$_2$Cl$_2$ (10 mL) and washed with saturated NaHCO$_3$ solution and brine and concentrated in vacuo. The residue obtained was purified by PTLC (silica gel, 1000 mm, EtOAc/hexane, 1:3) to yield 3a (30 mg, 51% overall from 1). $^1$H-NMR (400 MHz, CDCl$_3$): d 1.11 (s, 3H), 1.48–2.00 (m, 2H), 1.75 (s, 3H), 1.79 (s, 3H), 1.82 (s, 3H), 2.21 (s, 3H), 2.29 (s, 3H), 2.45–2.65 (m, 2H), 2.76 (d, J=5.4 Hz, 1H), 4.14 (d, J=8.2 Hz, 1H), 4.28–4.39 (m, 2H), 4.58 (d, J=8.5 Hz, 1H), 4.96 (d, J=8.7 Hz, 1H), 5.06 (d, J=10 Hz, 1H), 5.81 (d, J=8.8 Hz, 1H), 6.01 (m, 1H), 7.48 (d, J=8.1 Hz, 2H), 7.62 (t, J=8.2 Hz, 1H), 8.08 (d, J=7.1 Hz, 2H). $^{13}$C NMR (400 MHz, CDCl$_3$): d, 12.90, 15.34, 21.23, 22.69, 26.17, 26.87, 27.07, 31.72, 36.73, 38.43, 41.95, 42.31, 47.69, 69.42, 71.59, 72.19, 74.45, 76.37, 81.38, 83.66, 84.39, 107.39, 128.54, 129.56, 129.76, 133.19, 133.56, 139.64, 165.01, 169.13, 170.58.

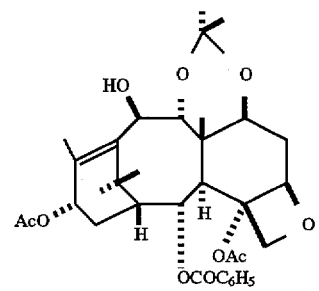

3a 7,9,10-Trideacetyl-10-triethylsilyl-baccatin VI 7,9-acetonide (4a): To a solution of 3a (30 mg, 0.049 mmol.) in dry CH$_2$Cl$_2$ (1 mL) was added imidazole (23.3 mg, 0.34 mmol.) followed by triethylsilyl chloride (50 mL, 0.29 mmol.). The mixture was stirred for 2 h at room temperature and then diluted with EtOAc (10 mL). The organic layer was washed with water and brine, dried over Na$_2$SO$_4$, and concentrated under reduced pressure. The residue thus obtained was purified by PTLC (silica gel, 1000 mm, EtOAc/hexane ¼) to yield 4a (26 mg, 74%). $^1$H-NMR (400 MHz, CDCl$_3$): d 0.65 (q, J=8.3 Hz, 6H), 0.99 (t, J=8.3 Hz, 9H), 1.18 (s, 3H), 1.46 (s, 3H), 1.61 (s, 3H), 1.65 (s, 3H), 1.82 (s, 3H), 1.84 (s, 3H), 1.88–1.95 (m, 2H), 2.18 (s, 3H), 2.25 9s, 3H), 2.41–2.65 (m, 2H), 2.70 (d, J=5.9 Hz, 1H), 4.13 (d, J=8.7 Hz, 1H), 4.27–4.36 (m, 2H), 4.86 (d, J=10.1 Hz, 1H), 4.95 (d, J=8.5 Hz, 1H), 5.85 (m, 1H), 5.95 (m, 1H), 7.48 (d, J=8.2 Hz, 2H), 7.61 (t, J=8.0 Hz, 1H), 8.07 (dd, J=1.3 and 8.2 Hz 2H). $^{13}$C NMR (400 MHz, CDCl$_3$): d 5.86, 7.15, 13.42, 15.20, 21.24, 22.71, 26.93, 27.03, 27.23, 28.23, 31.48, 38.51, 38.85, 42.62, 44.14, 48.21, 69.52, 71.81, 72.28, 74.17, 76.56, 81.30, 82.51, 84.43, 106.54, 128.55, 129.77, 133.46, 134.53, 137.23, 165.08, 169.19, 170.66.

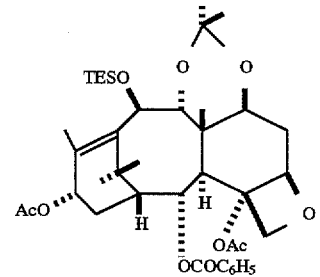

4a 7,9,10,13 -Tetradeacetyl-10-triethylsilylbaccatin VI 7,9-acetonide (5a): To a solution of 4a (26 mg, 0.035 mmol.) in THF (1.5 mL) was added methyllithium (75 mL, 1.4M solution in ether, 0.06 mmol.) at −78° C. and the solution stirred at the same temperature for 10 min. The mixture was quenched with saturated NH$_4$Cl, diluted with EtOAc (5 mL), and allowed to warm up to room temperature. The organic layer was washed with water and brine and dried over Na$_2$SO$_4$. The residue obtained after concentration of the organic layer under reduced pressure was purified by PTLC (silica gel, 500 mm, EtOAc/hexane 1:3) to yield 5a (9.5 mg, 63% on the basis of unrecovered starting compound) and starting material 4a (10.2 mg). $^1$H-NMR (400 MHz, CDCl$_3$): d 0.66 (q, J=8.4 Hz, 6H), 1.00 (t, J=8.4 Hz, 9H), 1.06 (s, 3H), 1.46 (s, 3H), 1.48 (s, 3H), 1.64 (s, 3H), 1.78 (s, 3H), 1.86–1.93 (m, 2H), 2.01 (s, 3H), 2.27 (s, 3H), 2.51–2.59 (m, 2H), 2.79 (d, J=5.9 Hz, 1H), 4.16 (d, J=8.8 Hz, 1H), 4.28–4.38 (m, 2H), 4.59 9m, 1H), 4.83 (d, J=10.4 Hz, 1H), 4.90 (d, J=8.4 Hz, 1H), 5.83 (m, 1H), 7.47 (t, J=8.4 Hz, 2H), 7.59 (t, J=8.3 Hz, 1H), 8.08 (dd, J=1.3 and 8.3 Hz, 2H). $^{13}$C NMR (400 MHz, CDCl$_3$) d 5.83, 7.15, 13.79, 15.56, 23.01, 26.64, 27.23, 28.20, 30.71, 31.37, 38.38, 38.66, 41.99, 44.35, 48.06, 67.88, 71.78, 71.91, 74.59, 81.95, 82.60, 84.90, 106.49, 128.55, 129.79, 129.87, 133.42, 133.90, 140.85, 165.11, 172.38.

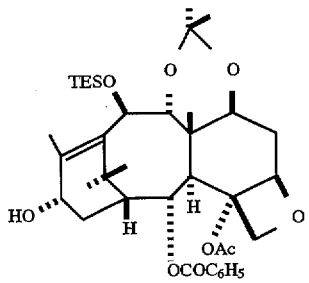

2'-Tetrabutyldimethylsilyl-10-deacetyl-1-deoxy-10-triethylsilyl-9-dihydro-9(R)-paclitaxel 7,9-acetonide (6a): To a solution of 5a (20 mg, 0.029 mmol.) in THF (1.0 mL) was added n-butyllithium (20 mL, 2M solution in hexane, 0.5 mmol) at −78° C., followed by addition of the β-lactam 8a (16 mg, 0.043 mmol) in dry THF (0.2 mL) and the solution stirred at the same temperature for 10 min. The mixture was then quenched with saturated $NH_4Cl$ at −10° C., diluted with EtOAc (5 mL), and allowed to warm to room temperature. The reaction mixture was then extracted with EtOAc (2×10 mL) and the organic layer was washed with water, brine and dried over $Na_2SO_4$. The residue obtained after concentration under reduced pressure was purified by PTLC (silica gel, 1000 mm, EtOAc/hexane 1:4) to yield 6a (7.2 mg, 23%). $^1$H-NMR (400 MHz, $CDCl_3$): d −0.15 (s, 3H), 0.01 (s, 3H), 0.65 (q, J=8.4 Hz, 6H), 0.82 (s, 9H), 1.00 (t, J=8.4 Hz, 9H), 1.21 (s, 3H), 1.46 (s, 3H), 1.52 (s, 3H), 1.68 (s, 3H), 1.71–2.00 (m, 2H), 1.84 (s, 3H), 1.86 (s, 3H), 2.38–2.65 (m, 2H), 2.48 (s, 3H), 2.74 (d, J=5.8 Hz, 1H), 4.18 (d, J=8.4 Hz, 1H), 4.34 (dd, J=9.1 and 8.0 Hz, 1H), 4.39 (m, 2H), 4.72 (s, 1H), 4.84 (d, J=9.2 Hz, 1H), 4.98 (d, J=8.6 Hz, 1H), 5.74 (d, J=8.2 Hz, 1H), 5.90 (m, 1H), 6.08 (m, 1H), 7.16 (d, J=7.0 Hz, 1H), 7.28–7.55 (m, 10H), 7.62 (t, J=8.4 Hz, 1H), 7.78 (d, J=8.2 Hz, 2H), 8.09 (dd, J=1.3 and 8.4 Hz, 2H). $^3$C NMR (400 MHz, $CDCl_3$): d −5.80, −5.17, 5.87, 7.15, 14.00, 14.78, 18.08, 23.44, 25.55, 26.36, 27.19, 27.51, 28.17, 31.68, 38.67, 38.92, 42.24, 44.22, 48.40, 55.63, 71.74, 71.99, 74.22, 74.80, 81.33, 82.61, 84.66, 106.50, 126.49, 126.98, 127.90, 128.62, 128.75, 129.62, 129.86, 131.73, 133.49, 134.24, 134.52, 136.96, 138.40, 165.25, 167.10, 169.61, 171.91.

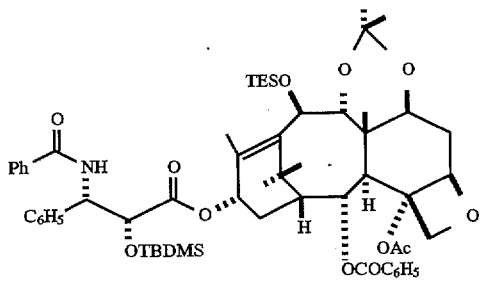

10-Deacetyl-1-deoxy-9(R)-dihydropaclitaxel 7,9-acetonide (7a): To a solution of 6a (7.0 mg, 0.006 mmol.) in THF (0.5 mL) and pyridine (100 mL) was added HF/pyridine (100 mL) and the mixture stirred at room temperature for 1.5 h. The reaction mixture was then diluted with EtOAc (5 mL) and the ethyl acetate layer washed successively with saturated $NaHCO_3$, 0.1N HCl, saturated $NaHCO_3$, water and brine. It was then dried over $Na_2SO_4$ and concentrated under reduced pressure. The residue obtained was purified by PTLC (silica gel, 500 mm, EtOAc/hexane 1:1) to yield 7a (6.0 mg, 99%). $^1$H-NMR (400 MHz, $CDCl_3$): d 1.16 (s, 3H), 1.52 (s, 6H), 1.56 (s, 3H), 1.69 (s, 3H), 1.78 (s, 3H), 1.81–1.98 (m, 2H), 2.28 (s, 3H), 2.58–2.66 (m, 2H), 2.71 (d, J=5.8 Hz, 1H), 3.78 (m, 1H), 4.18 (d, J=8.4 Hz, 1H), 4.21 (dd, J=9.1 and 8.0 Hz, 1H), 4.36 (m, 2H), 4.54 (d, J=10.2 Hz, 1H), 4.78 (m, 1H), 4.96 (m, 2H), 5.81 (m, 1H), 5.85–5.96 (m, 2H), 7.11–7.58 (m, 1H), 7.60 (t, J=8.3 Hz, 1H), 7.82 (d, J=8.4 Hz, 2H), 8.09 (dd, J=1.3 and 8.3 Hz, 2H). $^{13}$C NMR (400 MHz, $CDCl_3$) (12.99, 15.60, 22.60, 25.70, 26.87, 26.98, 31.75, 36.73, 38.34, 41.82, 42.56, 47.53, 54.44, 71.06, 71.31, 72.15, 73.79, 74.36, 76.43, 82.18, 83.63, 84.28, 107.51, 126.97, 127.07, 127.32, 128.06, 128.66, 128.88, 129.38, 129.77, 131.80, 133.68, 133.82, 134.25, 138.32, 138.35, 165.03, 166.30, 170.94, 171.32.

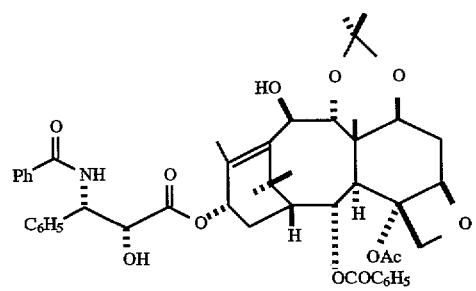

EXAMPLE 2

(Scheme 2)

Preparation of 10-Deacetyl-1-deoxy-9(R)-dihydrodocetaxel 7,9-benzylidene acetal (7b):

7,9,10-Trideacetylbaccatin VI 7,9-benzylidene acetal (3b): To a solution of the triol 2a (21.5 mg) in toluene (2 mL) camphor sulfonic acid (1 mg), molecular sieves (4A size) and benzaldehyde (0.2 mL, 1.96 mmol.) were added and the mixture was stirred at 40° C. for 15 h. The reaction mixture was filtered through a pad of Celite and washed with EtOAc. The organic layer was washed thoroughly with saturated $NaHCO_3$ solution and brine and dried over $Na_2SO_4$. The residue obtained after evaporation was purified by PTLC (silica gel, 1000 mm, EtOAc/hexane 2:3) to yield 3b (12 mg, 63% based on unrecovered starting material) and starting material 2a (5.5 mg). $^1$H-NMR (400 MHz, $CDCl_3$) d 1.19 (s, 3H), 1.65 (s, 3H), 1.79 (s, 3H), 1.64 and 1.96 (m, 1H each), 1.93 (s, 3H), 2.19 (s, 3H), 2.28 (s, 3H), 2.53 (s, 3H), 2.44–2.70 (m, 2H), 2.76 (d, J=5.4 Hz, 1H), 4.12 (d, J=8.2 Hz, 1H), 4.36 (d, J=8.5 Hz, 1H), 4.38 (d, J=8.9 Hz, 1H), 4.70 (d, J=10.1 Hz, 1H), 4.97 (d, J=8.7 Hz, 1H), 5.13 (s, 1H), 5.19 d, J=10 Hz, 1H), 5.80 (m, 1H), 6.00 (dd, J=8.8 and 8.7 Hz, 1H), 6.11 (s, 1H), 7.13–7.27 (m, 3H), 7.40–7.50 (m, 4H), 7.60 (m, 1H), 8.04 (d, J=7.1 Hz, 2H). $^{13}$C NMR, (400 MHz, $CDCl_3$): (13.13, 15.51, 21.25, 22.72, 26.04, 26.86, 31.71, 36.84, 38.23, 42.00, 42.46, 47.63, 69.42, 71.51, 71.54, 72.09, 81.38, 83.96, 84.44, 101.76, 125.26, 126.11, 128.19, 128.56, 128.61, 128.91, 129.00, 129.34, 129.52, 129.78, 133.04, 133.60, 137.80, 140.43, 165.00, 169.22, 170.59.

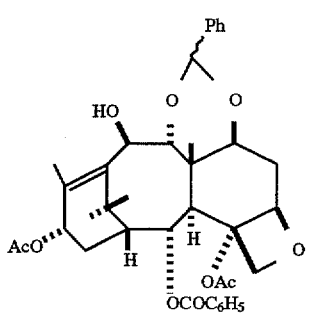

7,9,10-Trideacetyl-10-triethylsilylbaccatin VI 7,9-benzylidene acetal To a solution (4b): To a solution of 3b (12 mg, 0.018 mmol.) in dry DMF (1 mL) was added imidazole (11 mg, 0.16 mmol.) and triethylsilyl chloride (15 mL, 0.09 mmol.) at room temperature. The mixture was stirred overnight and diluted with EtOAc (10 mL). The organic layer was washed with water and brine, dried over $Na_2SO_4$, and concentrated under reduced pressure. The residue obtained was purified by PTLC (silica gel, 500 mm, EtOAc/hexane 1:3) to yield 4b (10.1 mg, 72%). $^1$H-NMR (400 MHz, $CDCl_3$) d 0.68 (q, J=8.4 Hz, 6H), 1.01 (t, J=8.4 Hz, 9H), 1.18 (s, 3H), 1.62 (m, 1H), 1.72 (s, 3H), 1.76 (s, 3H), 1.91 (s, 3H), 2.00 (s, 3H), 2.20 (s, 3H), 2.27 (s, 3H), 2.42–2.60 (m, 2H), 2.71 (d, J=5.9 Hz, 1H), 4.13 (d, J=8.7 Hz, 1H), 4.37 (m, 2H), 4.61 (d, J=10.5 Hz, 1H), 4.97 (d, J=8.5 Hz, 1H), 5.12 (d, J=10.2 Hz, 1H), 5.81–5.84 (dd, J=2.1 and 5.9 Hz, 1H), 5.97 (s, 1H), 5.99 (m, 1H), 7.36–7.61 (m, 8H), 8.06 (dd, J=1.3 and 8.5 Hz, 2H). $^{13}$C NMR (400 MHz, $CDCl_3$ (5.95, 7.10, 12.82, 15.47, 21.27, 22.72, 26.18, 26.92, 31.93, 38.36, 38.65, 43.07, 44.06, 47.81, 69.55, 71.62, 72.83, 76.29, 76.41, 81.54, 82.39, 84.68, 101.99, 126.41, 128.36, 128.54, 128.87, 129.7.

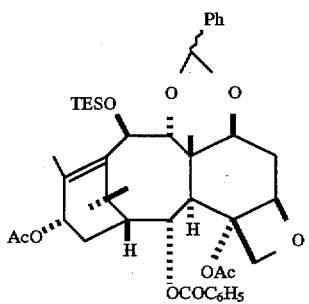

7,9,10,13-Tetradeacetyl-10-triethylsilylbaccatin VI 7,9-benzylidene acetal (5b): To a solution of 4b (16.3 mg, 0.021 mmol.) in THF (1.5 mL) was added methyllithium (100 mL, 1.4M solution in ether, 0.13 mmol.) at –78° C. and the solution stirred at the same temperature for 15 min. The mixture was quenched with buffer solution (pH 7.2) and diluted with EtOAc (5 mL). The organic layer was washed with water and brine, dried over $Na_2SO_4$, and concentrated under reduced pressure to give a residue which was purified by PTLC (silica gel, 500 mm, EtOAc/hexane 1/1) to provide 5b (5.5 mg, 37%) $^1$H-NMR (400 MHz, $CDCl_3$): d 0.68 (q, J=8.2 Hz, 6H), 1.02 (t, J=8.2 Hz, 9H), 1.55 (s, 3H), 1.68 (s, 3H), 1.75 (s, 3H), 1.91–2.22 (m, 2H), 2.07 (s, 3H), 2.27 (s, 3H), 2.56 (m, 2H), 2.89 (d, J=5.6 Hz, 1H), 4.16 (d, J=8.2 Hz, 1H), 4.37 (m, 2H), 4.60 (m, 2H), 4.93 (d, J=9.1 Hz, 1H), 5.12 (d, J=10.3 Hz, 1H), 5.81 (dd, J=2.4 and 6.2 Hz, 1H), 5.97 (s, 1H), 7.30–7.62 (m, 8H), 8.08 (dd, J=1.2 and 8.4 Hz, 2H). $^{13}$C NMR (400 MHz, $CDCl_3$) (5.94, 7.13, 12.85, 15.92, 22.97, 25.75, 30.52, 31.90, 38.00, 38.61, 42.75, 44.17, 47.63, 67.79, 71.58, 72.78, 82.01, 82.46, 84.91, 101.99, 126.45, 128.36, 128.54, 128.87, 129.78, 133.42, 134.15, 138.95, 142.07, 165.03, 171.88.

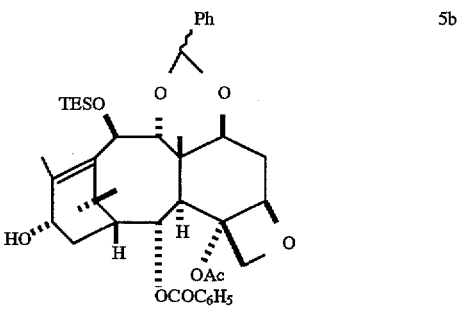

1-deoxy-10-triethylsilyl-9(R)-dihydrodocetaxel 7,9-benzylidene acetal (6b): To a solution of 5b (20 mg, 0.029 mmol.) and 8b (5.0 mg, 0.011 mmol.) in THF (1.0 mL) was added NaH (3.5 mg, 60% dispersion in mineral oil, 20 eq.) at 0° C. and the suspension allowed to stir at room temperature for 2.5 h. The mixture was then quenched with AcOH (0.2 mL) at 0° C. and diluted with EtOAc (5 mL). This reaction mixture was diluted with water and extracted with EtOAc (2×10 mL), and the organic layer was washed with a saturated solution of $NaHCO_3$, water and brine followed by drying over $Na_2SO_4$. The residue obtained after evaporation under reduced pressure was purified by PTLC (silica gel, 500 mm, EtOAc/hexane 1:4) to provide 6b (6.0 mg, 69%). $^1$H-NMR (400 MHz, $CDCl_3$): d 0.68 (q, J=8.2 Hz, 6H), 1.02 (t, J=8.2 Hz, 9H), 1.21 (s, 3H), 1.34 (s, 9H), 1.74 (s, 3H), 1.76 (s, 3H), 1.92 (s, 3H), 1.86–2.42 (m, 2H), 2.45 (s, 3H), 2.56 (m, 2H), 2.74 (d, J=5.6 Hz, 1H), 4.15 (d, J=8.3 Hz, 1H), 4.36–4.41 (m, 2H), 4.63 (d, J=10.2 Hz, 1H), 4.82 (s, 1H), 4.96 (d, J=8.8 Hz, 1H), 5.13 (d, J=10.2 Hz, 1H), 5.23 (d, J=9.7 Hz, 1H), 5.40 (d, J=10.5 Hz, 1H), 5.85 (dd, J=2.4 and 6.2 Hz, 1H), 5.95 (s, 1H), 7.27–7.60 (m, 13H), 8.08 (dd, J=1.2 and 8.4 Hz, 2H). $^{13}$C NMR (400 MHz, $CDCl_3$) d 5.99, 7.09, 12.59, 12.95, 14.98, 17.80, 17.86, 23.31, 26.34, 26.82, 28.16, 32.04, 38.62, 38.69, 43.00, 43.99, 48.05, 71.82, 72.68, 72.90, 76.00, 79.80, 81.62, 82.41, 84.88, 101.95, 126.43, 126.60, 127.61, 128.33, 128.46, 128.55, 128.84, 129.62, 129.87, 133.42, 134.12, 138.75, 139.03, 165.17, 169.40, 170.18, 172.33.

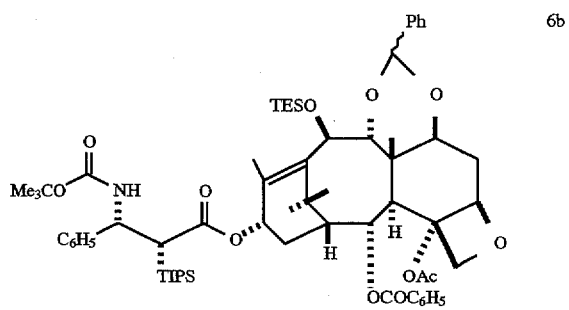

1-deoxy-9(R)-dihydrodocetaxel 7,9-benzylidene acetal (7b): To a solution of 6b (6.0 mg, 0.005 mmol.) in THF (1.0 mL) was added HF pyridine (200 mL) and the solution stirred at room temperature for 2 h. The reaction mixture was then diluted with EtOAc (15 mL) and the EtOAc layer washed successively with saturated $NaHCO_3$, 0.1N HCl, again with saturated $NaHCO_3$, water and brine. The resulting solution was dried over $Na_2SO_4$ and concentrated under reduced pressure and the residue obtained was purified by PTLC (silica gel, 500 mm, EtOAc/hexane 9:11) to yield 7b (1.5 mg, 33%). $^1$H-NMR (400 MHz, $CDCl_3$): d 1.16 (s, 3H), 1.39 (s, 9H), 1.52 (s, 3H), 1.65 (s, 3H), 1.78 (s, 3H), 1.79 (s, 3H), 1.91–2.00 (m, 2H), 2.25 (s, 3H), 2.62–2.66 (m, 2H), 2.74 (d, J=5.3 Hz, 1H), 4.01 (s, 1H), 4.15 (d, J=7.6 Hz, 1H), 4.30–4.36 (m, 2H), 4.62–4.68 (m, 2H), 4.93 (d, J=9.4 Hz, 1H), 4.96 (d, J=10.9 Hz, 1H), 5.15 (d, J=9.6 Hz, 1H), 5.29 (m, 1H), 5.60 (m, 1H), 5.80 (m, 1H), 5.91 (m, 1H), 6.12 (s, 1H), 7.28–7.60 (m, 13H), 8.04 (dd, J=1.2 and 8.6 Hz, 2H).

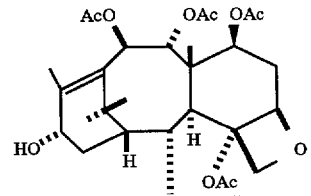

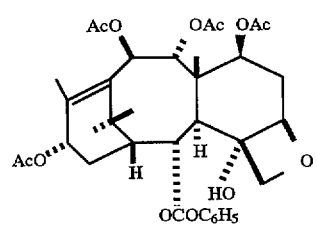

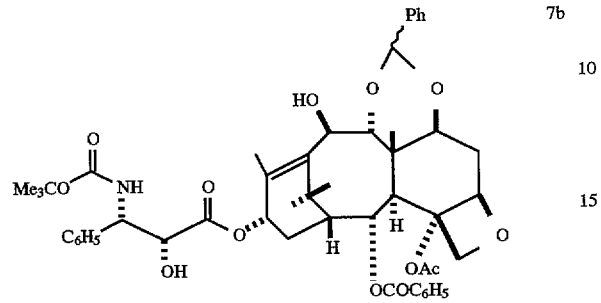

EXAMPLE 3

(Scheme 3)

Preparation of 7,9,10-Triacetyl-1-deoxy-9(R)-dihydrodocetaxel (7c):

13-Deacetyl-1-deoxybaccatin VI (2c) and 4-deacetyl-1-deoxybaccatin VI (2b): 1-Deoxybaccatin VI (1) (54 mg, 0.007 mmol.) was dissolved in THF (2 mL) and to this solution was added Red-Al (50 mL, 65% solution in toluene, 0.014 mmol) at −20° C. and the solution stirred for 20 min. The reaction mixture was quenched with a saturated solution of potassium tartrate (10 mL) and then diluted with EtOAc (15mL). The organic layer was washed with water and brine and dried over $Na_2SO_4$. Concentration under reduced pressure furnished crude product, which was purified by PTLC (silica gel, 1000 mm, EtOAc/hexane 1:1) to afford 2c (35 mg, 77%) and 2b (5.3 mg, 12%). Yields are calculated on the basis of unrecovered starting material; 6.0 mg of unreacted 1-deoxybaccatin VI (1) was recovered. 2c: $^1$H-NMR (400 MHz, CDCl$_3$): d 1.00 (s, 1H), 1.58 (s, 3H), 1.81 (s, 3H), 1.84–1.98 (m, 2H), 1.98 (s, 3H), 2.09 (s, 3H), 2.21 (s, 3H), 2.28 (s, 3H), 2.48–2.56 (m, 2H), 3.07 (d, J=6.1 Hz, 1H), 4.14 (d, J=8.2 Hz, 1H), 4.40 (d, J=8.4 Hz, 1H), 4.59 (m, 1H), 4.95 (d, J=8.7 Hz, 1H), 5.53–5.57 (dd, J=9.1 and 8.0 Hz, 1H), 5.84 (m, 1H), 5.98 (d, J=11.4 Hz, 1H), 6.15 (d, J=11.1 Hz, 1H), 7.47 (t, J=7.4 Hz, 2H), 7.60 (m, 1H), 8.08 (dd, J=1.3 and 8.4 Hz, 2H). $^{13}$C NMR (400 MHz, CDCl$_3$) d 12.85, 15.12, 20.78, 20.98, 21.40, 22.92, 26.59, 29.67, 30.06, 31.36, 34.61, 37.68, 44.06, 45.82, 47.10, 67.47, 71.39, 71.55, 71.88, 75.52, 81.65, 82.02, 128.57, 129.77, 132.74, 133.45, 141.95, 164.88, 169.09, 169.82, 170.12, 171.66. HRFABMS m/z (MNa$^+$) 679.2718; $C_{35}H_{44}O_{12}NNa$ requires 693.2761. 2b: $^1$H-NMR (400 MHz, CDCl$_3$) d 1.01 (s, 1H), 1.48 (s, 3H), 1.79 (s, 3H), 1.71–2.00 (m, 1H), 2.00 (s, 3H), 2.07 (s, 3H), 2.08 (s, 3H), 2.10 (s, 3H), 2.17 (s, 3H), 2.18–2.22 (m, 1H), 2.40 (m, 1H), 2.62–2.72 (m, 2H), 4.25 (d, J=7.7 Hz, 1H), 4.31 (d, J=8.0 Hz, 1H), 4.78–4.81 (dd, J=2.8 and 8.6 Hz, 1H), 5.29 (m, 1H), 5.65 (m, 1H), 5.91–5.95 (m, 2H), 6.06 (d, J=10.9 Hz, 1H), 7.46 (t, J=7.4 Hz, 2H) 7.59 (m, 1H), 8.01 (dd, J=1.4 and 8.4 Hz, 2H). $^{13}$C NMR (400 MHz, CDCl$_3$) d 13.06, 16.41, 20.68, 20.94, 21.19, 21.30, 25.47, 27.58, 33.31, 34.07, 37.34, 45.26, 46.35, 47.90, 69.48, 70.58, 71.24, 71.32, 74.91, 75.07, 79.45, 86.98, 128.63, 129.52, 129.71, 133.52, 136.25, 137.75, 164.90, 169.90, 169.21, 169.71, 169.98, 170.07. HRFABMS m/z (MNa$^+$) 679.2725; $C_{35}H_{44}O_{12}NNa$ requires 693.2761.

7,9,10-triacetyl-1-deoxy-9(R)-dihydro-2'-triisopropylsilyldocetaxel (6c): To a solution of 2c (30 mg, 0.045 mmol.) and the β-lactam 8b (23.0 mg, 0.054 mmol.) in THF (2.5 mL) was added NaH (23.0 mg, 60% dispersion in mineral oil, 22 eq.) at 0° C. and the suspension stirred at room temperature for 6 h. The mixture was then quenched with AcOH (1.0 mL) at 0° C., diluted with EtOAc (5 mL) and water (5 mL), and extracted with EtOAc (10 mL). The organic layer was washed with a saturated solution of NaHCO$_3$, water, and brine, and dried over Na$_2$SO$_4$. The residue obtained after concentration of the organic layer under reduced pressure was purified by PTLC (silica gel, 1000 mm, EtOAc hexane 3:7) to yield 6c (38 mg, 77%). $^1$H-NMR (400 MHz, CDCl$_3$): d 0.90–0.91 (m, 2H), 1.18 (s, 1H), 1.34 (s, 9H), 1.58 (s, 3H), 1.76–1.82 (m, 2H), 1.89 (s, 3H), 1.98 (s, 3H), 2.05 (s, 3H), 2.08 (s, 3H), 2.10 (s, 3H), 2.46 (s, 3H), 2.48–2.56 (m, 2H), 3.34 (d, J=5.9 Hz, 1H), 4.14 (d, J=8.3 Hz, 1H), 4.41 (d, J=8.0 Hz 1H), 4.81 (d, J=1.3 Hz, 1H), 4.98 (d, J=8.4 Hz, 1H), 5.24 (d, J=9.9 Hz, 1H), 5.42 (d, J=9.3 Hz, 1H), 5.56–5.61 (dd, J=7.9 and 9.6 Hz, 1H), 5.87–5.92 (m, 2H), 6.03 (d, J=11.4 Hz, 1H), 6.25 (d, J=11.2 Hz, 1H), 7.24–7.36 (m, 5H), 7.47 (t, J=7.7 Hz, 2H), 7.59 (m, 1H), 8.08 (dd, J=1.2 and 8.4 Hz, 2H). $^{13}$C NMR (400 MHz, CDCl$_3$): d 12.46, 12.56, 12.94, 14.95, 17.79, 17.89, 20.78, 20.92, 21.40, 23.26, 27.67, 28.16, 29.66, 31.36, 34.63, 38.21, 44.07, 45.66, 47.36, 70.81, 71.65, 71.88, 75.37, 75.55, 79.74, 81.36, 83.97, 126.51, 127.57, 128.45, 128.59, 129.53, 129.87, 132.86, 133.48, 165.02, 168.90, 169.15, 169.89, 170.12. HRFABMS m/z (MNa$^+$) 1098.5267; $C_{58}H_{81}NO_{16}Na$ requires 1098.5222.

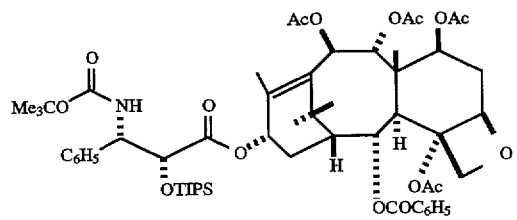

7,9,10-triacetyl-1-deoxy-9(R)-dihydrodocetaxel (7c): To a well stirred solution of 6c (12.0 mg, 0.011 mmol) in THF (1.2 mL) was added HF/pyridine (0.3 mL) and the solution stirred at room temperature for 3 h. The reaction mixture was then diluted with EtOAc (5 mL) and the EtOAc layer was washed successively with saturated NaHCO$_3$, 0.1N HCl, again with saturated NaHCO$_3$, water and brine. The resulting solution was dried over Na₂SO₄ and concentrated under reduced pressure and the residue obtained was purified by PTLC (silica gel, 500 mm, EtOAc/hexane 9:11) to furnish 7c (7.3 mg, 96% on the basis of unrecovered starting material) and starting material 6c (3.0 mg). $^1$H-NMR (400 MHz, CDCl₃): d 1.10 (s, 1H), 1.39 (s, 9H), 1.58 (s, 3H), 1.85 (s, 3H), 1.96–2.40 (m, 2H), 1.96 (s, 3H), 1.98 (s, 3H), 2.08 (s, 3H), 2.24 (s, 3H), 2.48–2.68 (m, 2H), 2.98 (d, J=5.8 Hz, 1H), 4.16 (m, 2H), 4.37 (d, J=8.2 Hz, 1H), 4.60 (s, 1H), 4.94 (d, J=8.1 Hz, 1H) 5.28 (m, 1H), 5.49 (dd, J=9.1 and 8.0 Hz, 1H), 5.63 (d, J=9.6 Hz, 1H), 5.86 (m, 2H), 5.97 (d, J=11.2 Hz, 1H), 6.14 (d, J=11.1 Hz, 1H), 7.26–7.48 (m, 7H), 7.58 (m, 1H), 8.05 (dd, J=1.2 and 8.4 Hz, 2H). $^{13}$C NMR (400 MHz, CDCl₃) d 12.98, 20.75, 20.90, 21.35, 22.51, 26.71, 28.25, 31.23, 34.57, 37.90, 43.97, 45.98, 47.18, 71.08, 71.63, 75.49, 77.78, 79.90, 81.89, 83.65, 126.97, 127.73, 128.52, 128.61, 129.47, 129.75, 133.59, 164.85, 168.90, 169.78, 170.04. HRMS m/z (M+Na)⁺ 942.3883; calcd for C₄₉H₆₁NO₁₆Na, 942.3888.

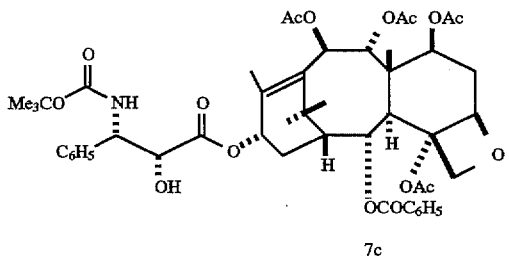

7c

EXAMPLE 4

(Scheme 3)

Preparation of 1-deoxy-9(R)-dihydrodocetaxel (7d):

1-deoxy-9(R)-dihydro-2'-triisopropylsilyldocetaxel (6d): To a solution of 7,9,10-triacetyl-1-deoxy-9(R)-dihydro-2'-triisopropylsilyldocetaxel (6c) (26 mg, 0.024 mmol.) in anhydrous CH₂Cl₂ (1.0 mL) was added benzyltrimethyl ammonium hydroxide (10 mL, 40% w/w solution in methanol, 0.024 mmol.) at 0° C. The reaction mixture was stirred at room temperature and the progress of the reaction was monitored by TLC, until a polar spot developed near the origin of the TLC plate. The reaction mixture was diluted with cold CH₂Cl₂ (5 mL) at 0° C. and quenched with 0.1N HCl (5 mL). The organic layer was separated, washed successively with water, saturated NaHCO₃, and brine, and dried over Na₂SO₄. Concentration of the organic layer under reduced pressure gave crude residue which was purified by PTLC (silica gel, 1000 mm, MeOH/CH₂Cl₂ 1:24) to furnish 6d (6.0 mg, 42% on the basis of unrecovered starting material) and starting compound 6c (10 mg). $^1$H-NMR (400 MHz, CDCl₃): d 0.91 (m, 2H), 1.25 (s, 3H), 1.35 (s, 9H), 1.78 (s, 3H), 1.79 (s, 3H), 1.87 (s, 3H), 1.91–2.04 (m, 2H), 2.45 (s, 3H), 2.49–2.61 (m, 2H), 2.91 (d, J=5.8 Hz, 1H), 4.17 (d, J=8.2 Hz, 1H), 4.35–4.42 (m, 2H), 4.79 (s, 1H), 4.92–4.98 (m, 2H), 5.23 (d, J=10.2 Hz, 1H), 5.77 (m, 1H), 5.94 (m, 1H), 7.24–7.36 (m, 5H), 7.47 (t, J=7.4 Hz, 2H), 7.59 (m, 1H), 8.05 (dd, J=1.3 and 8.5 Hz, 2H). $^{13}$C NMR (400 MHz, CDCl₃) d 12.56, 14.46, 17.79, 17.88, 23.36, 26.22, 27.50, 28.16, 38.16, 38.45, 43.87, 44.15, 45.88, 47.20, 47.43, 71.70, 71.90, 74.41, 75.45, 78.22, 79.18, 81.83, 84.09, 126.54, 127.61, 128.46, 128.59, 129.57, 129.86, 133.46, 148.62, 167.88, 169.28, 170.10.

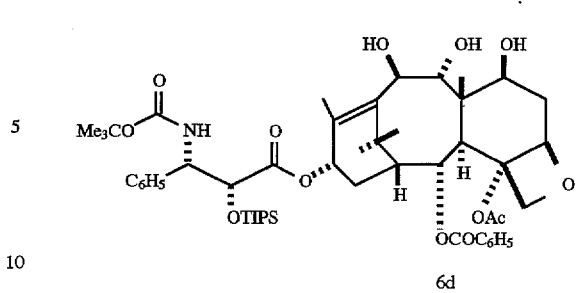

6d

1-Deoxy-9(R)-dihydrodocetaxel (7d): To a solution of 6d (3.0 mg, 0.003 mmol) in THF (1.0 mL) was added tetrabutyl ammonium fluoride (25 mL, 1M solution in THF) at –20° C. and the solution stirred at the same temperature for 5 min and at room temperature for 10 min. It was then diluted with EtOAc (5 mL) and this EtOAc layer was washed successively with saturated NaHCO₃, water, and brine, and dried over Na₂SO₄. The residue obtained after concentration of the organic layer was purified by PTLC (silica gel, 500 mm, EtOAc/hexane 3:2) to yield 7d (1.9 mg, 80%). $^1$H-NMR (400 MHz, CDCl₃) d 1.19 (s, 3H), 1.39 (s, 9H), 1.68 (s, 3H), 1.76 (s, 3H), 1.80 (s, 3H), 1.86–1.96 (m, 2H), 2.24 (s, 3H), 2.52–2.66 (m, 2H), 2.84 (d, J=5.3 Hz, 1H), 4.11 (m, 1H), 4.19 (d, J=8.5 Hz, 1H), 4.25–4.35 (m, 3H), 4.61 (s, 1H), 4.88 (d, J=10.2 Hz, 1H), 4.93 (d, J=8.3 Hz, 1H), 5.28 (d, J=9.4 Hz, 1H), 5.66 (d, J=9.6 Hz, 1H), 5.76 (m, 1H), 5.87 (m, 1H), 7.27–7.48 (m, 7H), 7.59 (t, J=7.4 Hz, 1H), 8.03 (dd, J=1.3 and 8.5 Hz, 2H).

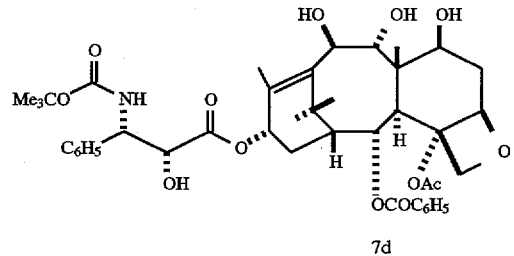

7d

EXAMPLE 5

(Scheme 4)

Preparation of 7,9-Diacetyl-1-deoxy-9(R)-dihydropaclitaxel (7e):

7,9-Diacetyl-1-deoxy-2'-triethylsilyl-9-(R)-Dihydropaclitaxel (6e): To a solution of 13-deacetyl-1-deoxybaccatin VI (2c) (10.0 mg, 0.015 mmol.) and the β-lactam 8c (R. Brieva, J. Z. Crich, C. J. Sih, "Chemoenzymatic Synthesis of the C-13 Side Chain of Taxol: Optically-Active 3-Hydroxy-4-phenyl β-Lactam Derivatives," *J. Org. Chem.*, 58 1068–1075, 1993) (9.3 mg, 0.022 mmol.) in THF (1.0 mL) was added NaH (7.0 mg, 60% dispersion in mineral oil, 20 eq.) at 0° C. and the mixture allowed to stir at room temperature for 2 h. The mixture was then quenched with AcOH (0.2 mL) at 0° C. and diluted with EtOAc (5 mL). This reaction mixture was diluted with water and extracted with EtOAc (2×10 mL), and the organic layer was washed with a saturated solution of NaHCO₃, water, and brine, followed by drying over Na₂SO₄. The residue obtained after evaporation under reduced pressure was purified by PTLC (silica gel, 500 mm, EtOAc/hexane ¼) to provide 7,9-diacetyl-1-deoxy-2'-triethylsilyl-9-(R)-dihydropaclitaxel (6e) (13.8 mg, 86%). $^1$H-NMR (400 MHz, CDCl$_3$): d 0.38–0.51 (m, 6H), 0.78–0.81 (m, 9H), 1.14 (s, 3H), 1.60 (s, 3H), 1.74–1.80 (m, 1H), 1.87 (s, 3H), 1.90–1.92 (m, 1H), 1.97 (s, 3H), 2.02–2.04 (m, 1H), 2.07 (s, 3H), 2.08 (s, 3H), 2.11 (s, 3H), 2.41–2.58 (m, 2H), 2.49 (s, 3H), 3.03 (d, J=5.50 Hz, 1H), 4.15 (d, J=8.39 Hz, 1H), 4.40 (d, J=8.24 Hz, 1H), 4.72 (d, J=1.83 Hz, 1H), 4.99 (d, J=8.39 Hz, 1H), 5.57 (dd, J=9.31 and 7.93 Hz, 1H), 5.66 (d, J=8.7 Hz, 1H), 5.89 (m, 1H), 5.99–6.04 (m, 2H), 6.24 (d, J=11.29 Hz, 1H), 7.14 (d, J=8.7 Hz, 1H), 7.29–7.51 (m, 10H), 7.60 (t, J=7.47 Hz, 1H), 7.74 (d, J=7.02 Hz, 2H), 8.07 (d, J=7.17 Hz, 2H). $^{13}$C NMR (400 MHz, CDCl$_3$): d 4.36, 6.49, 12.99, 14.43, 20.78, 20.93, 21.42, 23.33, 27.53, 31.40, 34.67, 38.25, 44.06, 45.75, 47.32, 55.63, 71.40, 71.46, 71.88, 74.41, 75.56, 81.35, 83.88, 126.53, 127.01, 127.80, 128.58, 128.65, 129.43, 129.86, 131.65, 133.28, 133.54, 134.27, 138.42, 138.52, 165.02, 167.17, 168.97, 169.34, 169.97, 170.07, 171.95. HRFABMS m/z (MH$^+$) 1038.4657; C$_{57}$H$_{72}$NO$_{15}$Si requires 1038.4671.

7,9-Diacetyl-1-deoxy-9(R)-dihydropaclitaxel (7e): To a solution of 6e (11.0 mg, 0.010 mmol.) in THF (1 mL) and pyridine (100 mL) was added HF/pyridine (100 mL) and the mixture stirred at room temperature for 30 min. The mixture was then diluted with EtOAc (5 mL) and this ethyl acetate layer was washed successively with saturated NaHCO$_3$, 0.1N HCl, again with saturated NaHCO$_3$, water, and brine, and dried over Na$_2$SO$_4$. The residue obtained after evaporation was purified by PTLC (silica gel, 500 mm, EtOAc/hexane 1/1) to yield 7,9-diacetyl-1-deoxy-9(R)-dihydropaclitaxel 7e (8.11 mg, 87%). $^1$H-NMR (400 MHz, CDCl$_3$): d 1.08 (s, 3H), 1.58 (s, 6H), 1.84 (s, 3H), 1.86–1.90 (m, 2H), 1.96 (s, 3H), 2.00–2.02 (m, 2H), 2.08 (s, 3H), 2.10 (s, 3H), 2.28 (s, 3H), 2.53–2.68 (m, 2H), 2.96 (d, J=5.80 Hz, 1H), 4.16 (d, J=8.09 Hz, 1H), 4.38 (d, J=8.24 Hz, 1H), 4.42 (dd, J=1.68 and 2.4 Hz, 1H), 4.74 (dd, J=2.59 and 2.44 Hz, 1H), 4.96 (d, J=8.09 Hz, 1H), 5.47 (dd, J=8.70 and 8.39 Hz, 1H), 5.85–5.87 (m, 3H), 5.96 (d, J=11.14 Hz, 1H), 6.10 (d, J=11.14 Hz, 1H), 7.32–7.51 (m, 10H), 7.60 (t, J=7.47 Hz, 1H), 7.81 (d, J=7.05 Hz, 2H), 8.06 (d, J=7.18 Hz, 2H). $^{13}$C NMR (400 MHz, CDCl$_3$): d 12.97, 15.23, 20.74, 20.90, 21.36, 22.60, 26.59, 26.69, 31.31, 34.57, 37.87, 43.99, 45.99, 47.09, 54.27, 70.81, 70.94, 71.59, 73.90, 75.44, 82.00, 83.62, 126.98, 127.23, 127.99, 128.62, 128.65, 129.43, 129.73, 131.76, 133.62, 133.79, 134.21, 137.48, 138.49, 164.83, 166.35, 168.95, 169.81, 170.02, 170.94, 171.08. HRFABMS m/z (MFNa$^+$) 946.3655; C$_{51}$H$_{57}$NO$_{15}$Na requires 946.3625.

Following the procedures described above, together with procedures that are common in the art, such as those described in Klein et al., J. Med. Chem., 38, pp 1482–1492 (1995), the following compounds III within the scope of this invention, can be synthesized.

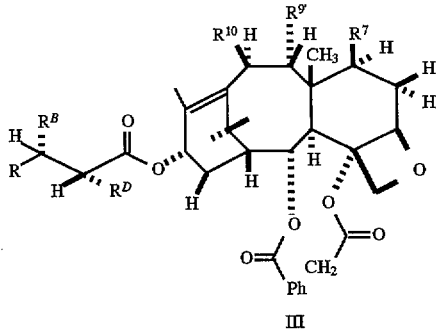

III

| R | R$^B$ | R$^{10}$ | R$^{9'}$ | R$^7$ |
|---|---|---|---|---|
| Phenyl | tBuOCO(O)NH— | HO— | HO— | CH$_3$O— |
| Phenyl | tBuOCO(O)NH— | HO— | CH$_3$O— | HO |
| Phenyl | tBuOCO(O)NH— | AcO— | HO— | CH$_3$O— |
| Phenyl | tBuOCO(O)NH— | AcO— | CH$_3$O— | HO |
| Phenyl | iPrOCO(O)NH— | HO— | HO— | CH$_3$O— |
| Phenyl | iPrOCO(O)NH— | HO— | CH$_3$O— | HO |
| Phenyl | iPrOCO(O)NH— | AcO— | HO— | CH$_3$O— |
| Phenyl | iPrOCO(O)NH— | AcO— | CH$_3$O— | HO |
| Phenyl | nBuOCO(O)NH— | HO— | HO— | CH$_3$O— |
| Phenyl | nBuOCO(O)NH— | HO— | CH$_3$O— | HO |
| Phenyl | nBuOCO(O)NH— | AcO— | HO— | CH$_3$O— |
| Phenyl | nBuOCO(O)NH— | AcO— | CH$_3$O— | HO |
| Phenyl | PhC(O)NH— | HO— | HO— | CH$_3$O— |
| Phenyl | PhC(O)NH— | HO— | CH$_3$O— | HO |
| Phenyl | PhC(O)NH— | AcO— | HO— | CH$_3$O— |
| Phenyl | PhC(O)NH— | AcO— | CH$_3$O— | HO |
| isobutyl— | tBuOCO(O)NH— | HO— | HO— | CH$_3$O— |
| isobutyl— | tBuOCO(O)NH— | HO— | CH$_3$O— | HO |
| isobutyl— | tBuOCO(O)NH— | AcO— | HO— | CH$_3$O— |
| isobutyl— | tBuOCO(O)NH— | AcO— | CH$_3$O— | HO |
| isobutyl— | iPrOCO(O)NH— | HO— | HO— | CH$_3$O— |
| isobutyl— | iPrOCO(O)NH— | HO— | CH$_3$O— | HO |
| isobutyl— | iPrOCO(O)NH— | AcO— | HO— | CH$_3$O— |
| isobutyl— | iPrOCO(O)NH— | AcO— | CH$_3$O— | HO |
| isobutyl— | nBuOCO(O)NH— | HO— | HO— | CH$_3$O— |
| isobutyl— | nBuOCO(O)NH— | HO— | CH$_3$O— | HO |
| isobutyl— | nBuOCO(O)NH— | AcO— | HO— | CH$_3$O— |
| isobutyl— | nBuOCO(O)NH— | AcO— | CH$_3$O— | HO |
| isobutyl— | PhC(O)NH— | HO— | HO— | CH$_3$O— |
| isobutyl— | PhC(O)NH— | HO— | CH$_3$O— | HO |
| isobutyl— | PhC(O)NH— | AcO— | HO— | CH$_3$O— |
| isobutyl— | PhC(O)NH— | AcO— | CH$_3$O— | HO |
| isobutenyl— | tBuOCO(O)NH— | HO— | HO— | CH$_3$O— |
| isobutenyl— | tBuOCO(O)NH— | HO— | CH$_3$O— | HO |
| isobutenyl— | tBuOCO(O)NH— | AcO— | HO— | CH$_3$O— |
| isobutenyl— | tBuOCO(O)NH— | AcO— | CH$_3$O— | HO |
| isobutenyl— | iPrOCO(O)NH— | HO— | HO— | CH$_3$O— |
| isobutenyl— | iPrOCO(O)NH— | HO— | CH$_3$O— | HO |
| isobutenyl— | iPrOCO(O)NH— | AcO— | HO— | CH$_3$O— |
| isobutenyl— | iPrOCO(O)NH— | AcO— | CH$_3$O— | HO |
| isobutenyl— | nBuOCO(O)NH— | HO— | HO— | CH$_3$O— |
| isobutenyl— | nBuOCO(O)NH— | HO— | CH$_3$O— | HO |
| isobutenyl— | nBuOCO(O)NH— | AcO— | HO— | CH$_3$O— |
| isobutenyl— | nBuOCO(O)NH— | AcO— | CH$_3$O— | HO |
| isobutenyl— | PhC(O)NH— | HO— | HO— | CH$_3$O— |
| isobutenyl— | PhC(O)NH— | HO— | CH$_3$O— | HO |
| isobutenyl— | PhC(O)NH— | AcO— | HO— | CH$_3$O— |
| isobutenyl— | PhC(O)NH— | AcO— | CH$_3$O— | HO |
| 3'-p-F—Ph | tBuOCO(O)NH— | HO— | HO— | CH$_3$O— |
| 3'-p-F—Ph | tBuOCO(O)NH— | HO— | CH$_3$O— | HO |
| 3'-p-F—Ph | tBuOCO(O)NH— | AcO— | HO— | CH$_3$O— |
| 3'-p-F—Ph | tBuOCO(O)NH— | AcO— | CH$_3$O— | HO— |
| 3'-p-F—Ph | iPrOCO(O)NH— | HO— | HO— | CH$_3$O— |
| 3'-p-F—Ph | iPrOCO(O)NH— | HO— | CH$_3$O— | HO |
| 3'-p-F—Ph | iPrOCO(O)NH— | AcO— | HO— | CH$_3$O— |
| 3'-p-F—Ph | iPrOCO(O)NH— | AcO— | CH$_3$O— | HO |
| 3'-p-F—Ph | nBuOCO(O)NH— | HO— | HO— | CH$_3$O— |
| 3'-p-F—Ph | nBuOCO(O)NH— | HO— | CH$_3$O— | HO |
| 3'-p-F—Ph | nBuOCO(O)NH— | AcO— | HO— | CH$_3$O— |
| 3'-p-F—Ph | nBuOCO(O)NH— | AcO— | CH$_3$O— | HO |
| 3'-p-F—Ph | PhC(O)NH— | HO— | HO— | CH$_3$O— |

-continued

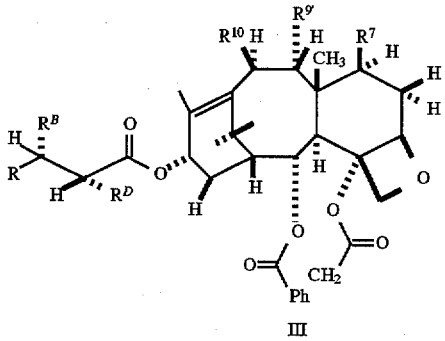

III

| R | R$^B$ | R$^{10}$ | R$^{9'}$ | R$^7$ |
|---|---|---|---|---|
| 3'-p-F—Ph | PhC(O)NH— | HO— | CH$_3$O— | HO |
| 3'-p-F—Ph | PhC(O)NH— | AcO— | HO— | CH$_3$O— |
| 3'-p-F—Ph | PhC(O)NH— | AcO— | CH$_3$O— | HO |

The compounds of this invention exhibit antitumor activities in in vivo and/or in vitro models. For example, the following test describes the in vitro test used to evaluate some representative compounds of this invention.

In Vitro Cytotoxicity Test

The C-1 deoxy taxane derivatives possess cytotoxicity in vitro against human colon carcinoma cells HCT-116 and against a paclitaxel-resistant cell line HCT116/VM46. Cytotoxicity was assessed in HCT-116 and line HCT116/VM46 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, el. al., "Comparison of MTT, XTT, and a novel tetrazolium compound MTS for in vitro proliferation and chemosensitivity assays.," *Mol. Biol. Cell* 3 (Suppl.):184a, 1992. Cells were plated at 4,000 cell/well in 96 well microliter plates and 24 hours later drugs were added and serial diluted. The cells were incubated at 37° for 72 hours at which time the tetrazolium dye, MTS at 333 µg/ml (final concentration), in combination with the electron coupling agent phenazine methosulfate at 25 µM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an IC$_{50}$, which is the drug concentration required to inhibit cell proliferation (i.e. absorbance at 450 nM) to 50% of that of untreated control cells. The IC$_{50}$ values for compounds evaluated in this assay are evaluated in Table I.

TABLE I

| | Cytotoxicity Assay IC$_{50}$ (nM) against HCT 116 Human colon tumor cell line[1] | |
|---|---|---|
| Compound | HCT 116 | HCT/VM46 |
| 7a | 0.0043 nM | 0.0115 nM |
| 7b | 0.0105 nM | 0.0296 nM |
| 7c | 0.0046 nM | 0.0218 nM |
| 7d | N.A. | N.A. |
| paclitaxel | 0.0016 nM | 0.225 nM |

[1]Cytotoxicity was determined after a 72 h exposure by MTS assay.

The compounds of this invention show significantly improved activity against the paclitaxel-resistant cell line HVT/VM46 than does paclitaxel itself. These compounds thus provide significant and unexpected improvement in paclitaxel-like cytotoxic activity. Consequently, we expect that these compounds will possess substantially improved anti-tumor activity.

The present invention provides compounds useful as active agents in effecting an antitumor or antineoplastic effect in a tumor-bearing host. These compounds or their pharmaceutically acceptable salts can be compounded into pharmaceutical formulations for administration to cancer patients. Such formulations will comprise one or more of the active agents of the present invention in combination with pharmaceutically acceptable excipients and/or adjuvants. Contemplated routes of administration are parenteral and oral.

The present invention further provides a method for inhibiting, reducing, or eliminating tumors comprising administering to a mammalian, especially human, tumor bearing host an antitumor effective amount of a compound of formula I.

For treating a variety of tumors, the compounds of formula I of the present invention will be used in a manner similar to that of paclitaxel, see e.g. Physician's Desk Reference, 49th Edition, Medical Economics, p 682, 1995. The dosage, mode and schedule of administration for the compounds of this invention are not particularly restricted; an oncologist skilled in the art of cancer treatment will be able to ascertain, without undue experimentation, an appropriate treatment protocol for administering the compound of the present invention. Thus the compounds of formula I will be administered via any suitable route of administration, parenterally or orally. Parenteral administration includes intravenous, intraperitoneal, intramuscular, and subcutaneous administration.

The doses utilized to implement the methods of the present invention will be similar to those used in administering paclitaxel, taking into account the enhanced activity of the present compounds. It is expected that one of ordinary skill in the art will be able to discern suitable anti-tumor effective doses and regimens for the efficacious administration of the present anti-cancer agents. It will be understood that such doses vary, depending on the type of administration, the particular product selected, and the profile and particular characteristics of the patient to be treated. The desired doses will be those that are therapeutically effective for the treatment of disorders caused by abnormal cell proliferation. The compounds of the present invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m$^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. For example, paclitaxel is formulated for parenteral administration in polyethoxylated castor oil (Cremophor®). Examples of formulating paclitaxel or derivatives thereof are also found in, for example, U.S. Pat. Nos. 4,960,790 and 4,814,470, and such examples can be followed to formulate the compounds of this invention. For example, compounds of formula I might be formulated in the form of tablets, pills, powder mixtures, capsules, injectables, storage stable solutions, suppositories, emulsions, dispersions, food premix, and in other suitable forms. It might also be manufactured in the form of sterile solid compositions, for example, freeze dried (lyophilized) and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use in parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

SCHEME 1

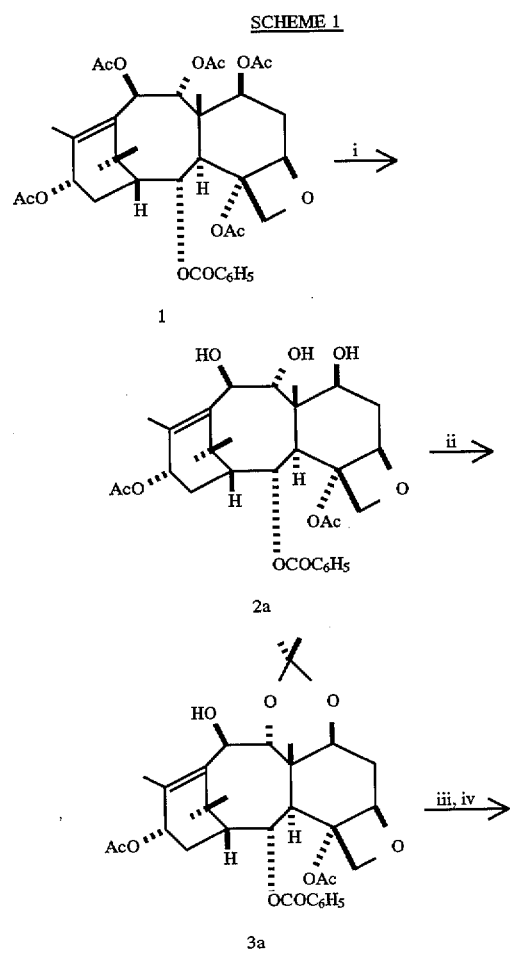

-continued
SCHEME 1

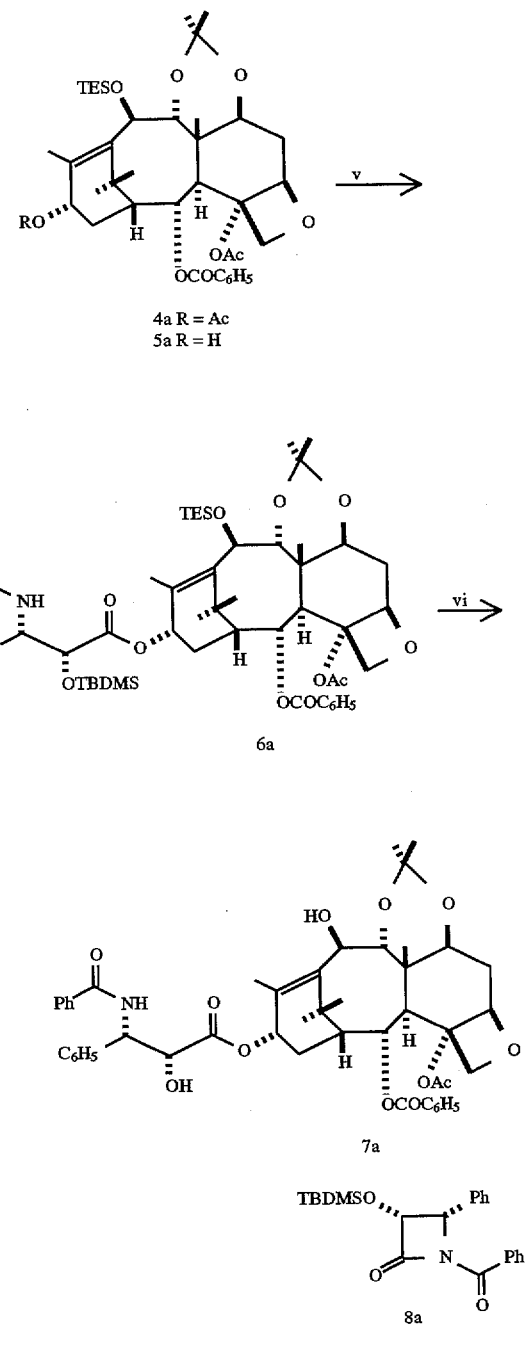

Reagents:
i. Triton B, CH₂Cl₂, 65% or 1N NaOH/MeOH, 84%
ii. 2-Methoxypropene, PPTS, CH₂Cl₂, 55%
iii. TESCl, Imidazole, CH₂Cl₂, 74%
iv. MeLi, THF, 63%
v. 8a, n-BuLi, THF, 23%
vi. HF, pyridine, THF, 99%

SCHEME 2
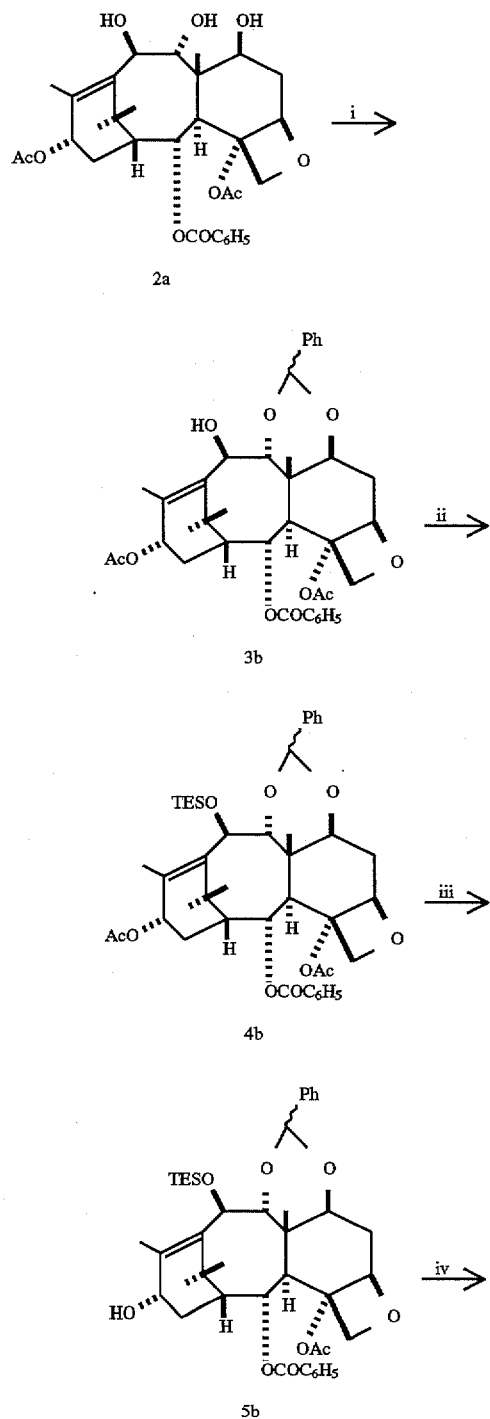
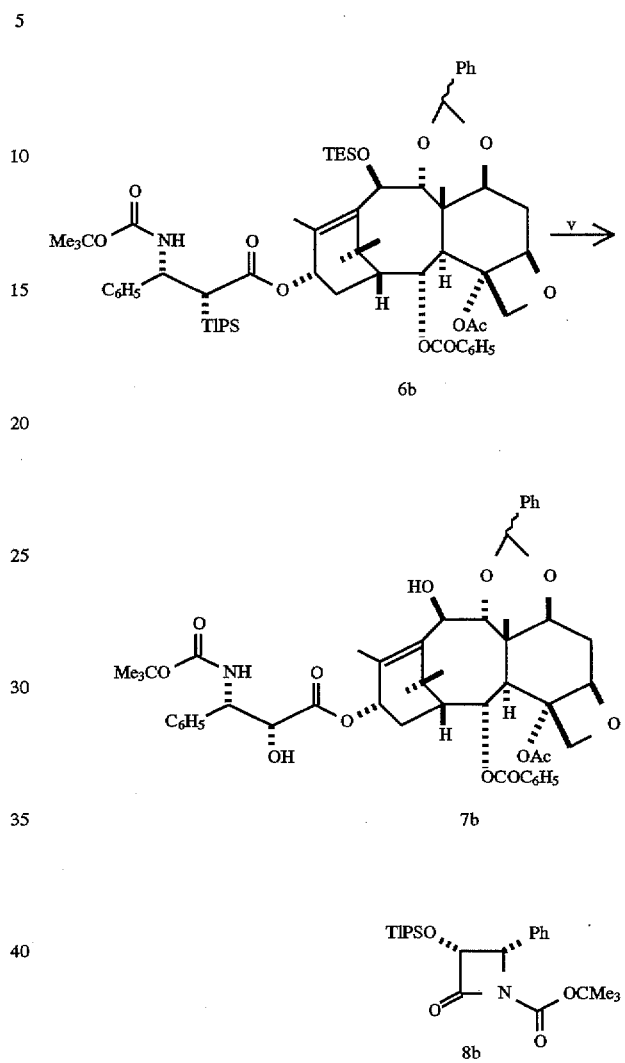
Reagents:
i. PhCHO, CSA, Toluene, 63%
ii. TESCl, Imidazole, CH$_2$Cl$_2$, 72%
iii. MeLi, THF, 37%
iv. 8b, NaH, THF, 69%
v. HF, pyridine, THF, 33%

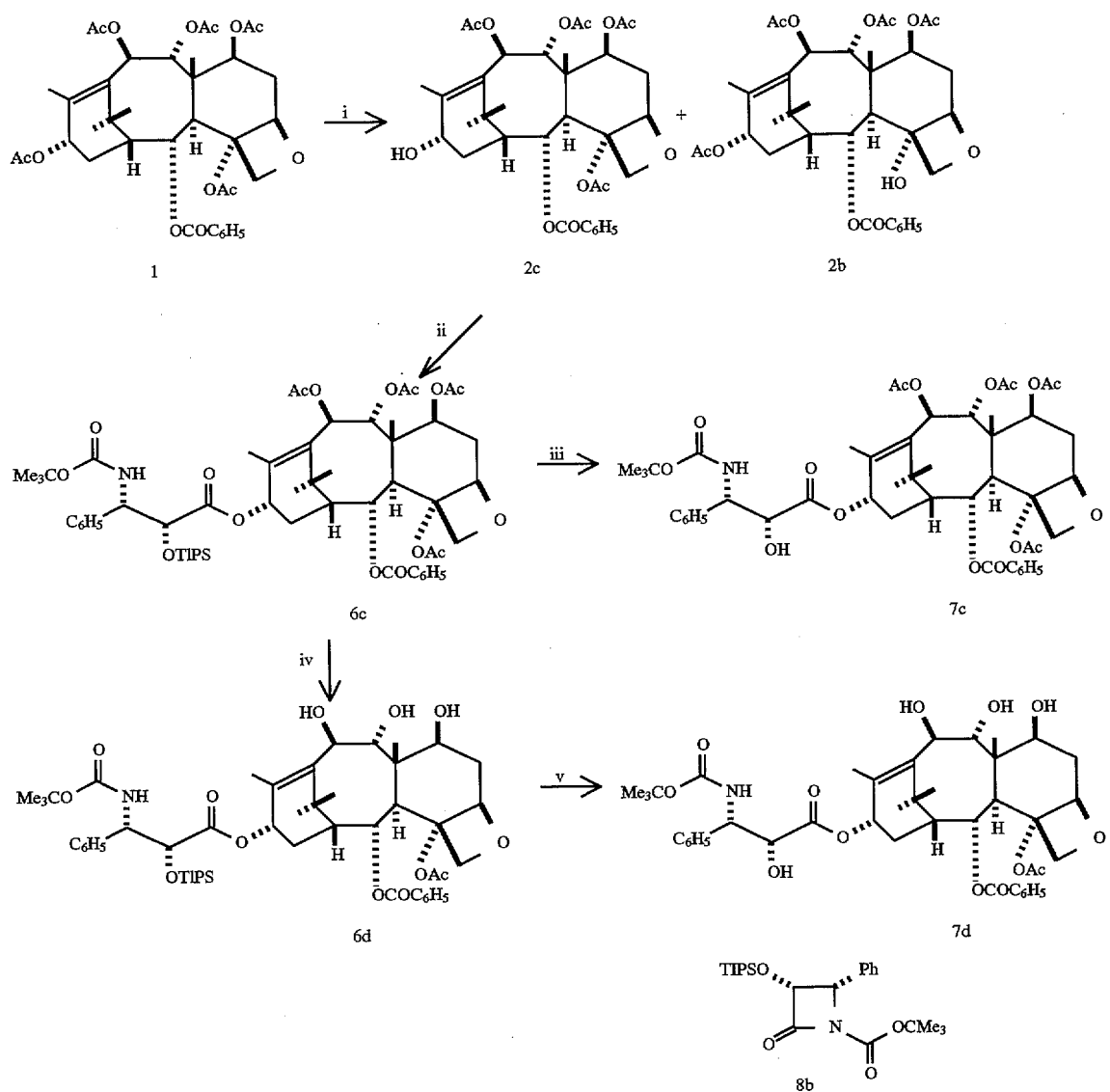
SCHEME 3
Reagents:
i. Red Al, THF, 77%
ii. 8b, NaH, THF, 77%
iii. HF, pyridine, THF, 96%
iv. Triton B, CH$_2$Cl$_2$, 42%
v. TBAF, THF, 80%

SCHEME 4

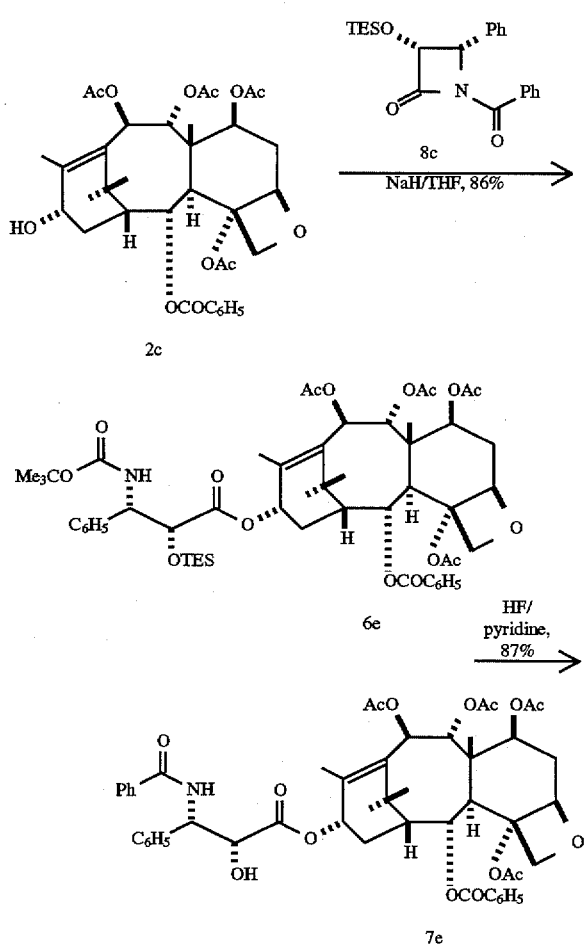

What is claimed is:

1. A method for preparing 1-deoxy-7,9-acetonide paclitaxel analogues comprising:
   a. deacetylating 1-deoxybaccatin VI to form a 7,9,10-trisdeacetyl derivative;
   b. modifying the 7,9,10-trisdeacetyl derivative to form a 7,9-acetonide derivative;
   c. protecting an hydroxy substituent at C-10 of 1-deoxybaccatin VI with a hydroxy protecting group;
   d. forming a C-13 deacetyl derivative of the product of step c;
   e. esterifying the C-13 deacetyl derivative of step d by reaction with a 3-hydroxy-4-phenyl β-lactam, wherein the 3-hydroxy group is protected with a protecting group; and
   f. deprotecting both the C-2' position resulting from step e, and the C-10 position.

2. The method of claim 1, wherein the β-lactam is N-t-butoxy-3-triisopropylsilyloxy-4-phenyl β-lactam.

3. The method of claim 1, wherein the hydroxy protecting groups of steps c and e are the same or different and are trialkylsilyl protecting groups.

4. The method of claim 1, wherein the acetonide of step b is formed by reacting the product of step a with 2-methoxypropene.

5. A method for preparing 1-deoxy-7,9-benzylidene acetal paclitaxel analogues comprising:
   a. deacetylating 1-deoxybaccatin VI to form a 7,9,10-trisdeacetyl derivative;
   b. modifying the 7,9,10-trisdeacetyl derivative to form a 7,9-benzylidene acetal derivative;
   c. protecting an hydroxy substituent at C-10 of 1-deoxybaccatin VI with a hydroxy protecting group;
   d. forming a C-13 deacetyl derivative of the product of step c;
   e. esterifying at the C-13 position of the deacetyl derivative of step d by reaction with a 3-hydroxy-4-phenyl β-lactam, wherein the 3-hydroxy substituent is protected with a hydroxy protecting group; and
   f. deprotecting both the C-2' position resulting from step e, and the C-10 position.

6. The method of claim 5, wherein the β-lactam is N-t-butoxy-3-tetrabutyldimethylsilyloxy-4-phenyl β-lactam.

7. The method of claim 5, wherein the hydroxy protecting groups of steps c and e are the same or different and are trialkylsilyl protecting groups.

8. The method of claim 5, wherein the 7,9-benzylidene acetal of step b is formed by reacting the product of step a with benzaldehyde.

9. A method for forming 1-deoxy docetaxel comprising:
   a. selectively cleaving an acetoxy group from C-13 of 1-deoxybaccatin VI to form 13-deacetyl-1-deoxybaccatin VI;
   b. coupling the product of step a with a 3-silyl ester-4-phenyl β-lactam to form a C-13 ester; and
   c. deacetylating the 7, 9, and 10 positions of the product of step b.

10. The method of claim 9, wherein the β-lactam is N-t-butoxy-3-tetrabutyldimethylsilyloxy-4-phenyl β-lactam.

11. A method for forming 7,9-diacetyl-1-deoxy-9(R)-dihydropaclitaxel comprising:
    a. selectively cleaving an acetoxy group from C-13 of 1-deoxybaccatin VI to form 13-deacetyl-1-deoxybaccatin VI;
    b. coupling the product of step a with N-benzyl-3-triethylsilyloxy-4-phenyl β-lactam to form an ester at C-13; and
    c. selectively removing the triethylsilyl hydroxy protecting group from C-2' of the product of step b.

* * * * *